United States Patent
Stoll et al.

(10) Patent No.: US 12,258,587 B2
(45) Date of Patent: Mar. 25, 2025

(54) COMPOSITIONS AND METHODS FOR INTERNAL CONTROLS OF MICROVESICLE ISOLATIONS

(71) Applicant: Exosome Diagnostics, Inc., Waltham, MA (US)

(72) Inventors: Georg Stoll, Munich (DE); Daniel Enderle, Martinsried (DE); Mikkel Noerholm, Martinsried (DE); Johan Karl Olov Skog, Lincoln, MA (US)

(73) Assignee: Exosome Diagnostics, Inc., Waltham, MA (US)

( * ) Notice: Subject to any disclaimer, the term of this patent is extended or adjusted under 35 U.S.C. 154(b) by 858 days.

(21) Appl. No.: 17/295,287

(22) PCT Filed: Nov. 20, 2019

(86) PCT No.: PCT/US2019/062429
§ 371 (c)(1),
(2) Date: May 19, 2021

(87) PCT Pub. No.: WO2020/106853
PCT Pub. Date: May 28, 2020

(65) Prior Publication Data
US 2021/0403881 A1 Dec. 30, 2021

Related U.S. Application Data

(60) Provisional application No. 62/769,745, filed on Nov. 20, 2018.

(51) Int. Cl.
| | | |
|---|---|---|
| C12N 15/10 | (2006.01) | |
| C12N 7/00 | (2006.01) | |
| C12Q 1/6806 | (2018.01) | |
| C12Q 1/6851 | (2018.01) | |
| C12Q 1/70 | (2006.01) | |

(52) U.S. Cl.
CPC .......... *C12N 7/00* (2013.01); *C12N 15/1003* (2013.01); *C12Q 1/6806* (2013.01); *C12Q 1/6851* (2013.01); *C12Q 1/70* (2013.01); *C12N 2770/24251* (2013.01); *C12N 2770/24351* (2013.01)

(58) Field of Classification Search
CPC .......... C12N 2770/20051; C12N 2770/24351; C12N 7/00; C12N 15/1003; C12N 2770/24251; C12Q 1/6806; C12Q 1/6851; C12Q 1/70; C12Q 2545/101; C12Q 2600/118; C12Q 2600/166; C12Q 2563/161
See application file for complete search history.

(56) References Cited

U.S. PATENT DOCUMENTS

| | | |
|---|---|---|
| 5,219,727 A | 6/1993 | Wang et al. |
| 5,538,871 A | 7/1996 | Nuovo et al. |
| 5,556,773 A | 9/1996 | Yourno |
| 5,582,981 A | 12/1996 | Toole et al. |
| 5,639,606 A | 6/1997 | Willey |
| 5,639,611 A | 6/1997 | Wallace et al. |
| 5,840,867 A | 11/1998 | Toole et al. |
| 6,004,755 A | 12/1999 | Wang |
| 6,525,154 B1 | 2/2003 | Shea et al. |
| 6,812,023 B1 | 11/2004 | Lamparski et al. |
| 6,893,837 B2 | 5/2005 | Slamon et al. |
| 6,899,863 B1 | 5/2005 | Dhellin et al. |
| 6,913,879 B1 | 7/2005 | Schena |
| 6,994,960 B1 | 2/2006 | Foote et al. |
| 7,074,563 B2 | 7/2006 | Koster |
| 7,186,512 B2 | 3/2007 | Martienssen et al. |
| 7,198,893 B1 | 4/2007 | Koster et al. |
| 7,198,923 B1 | 4/2007 | Abrignani et al. |
| 7,332,553 B2 | 2/2008 | Sellergren et al. |
| 7,364,848 B2 | 4/2008 | Van Beuningen et al. |
| 7,378,245 B2 | 5/2008 | Liu |
| 7,384,589 B2 | 6/2008 | Hart et al. |
| 11,136,627 B2 * | 10/2021 | Noerholm ............ C12N 7/00 |
| 2010/0196426 A1 | 8/2010 | Skog et al. |
| 2010/0331240 A1 | 12/2010 | Michelow et al. |
| 2011/0195426 A1 | 8/2011 | Russo et al. |
| 2015/0010951 A1 | 1/2015 | LaPointe et al. |
| 2016/0312211 A1 * | 10/2016 | Noerholm ............ C12N 7/00 |
| 2021/0388453 A1 | 12/2021 | Noerholm et al. |

FOREIGN PATENT DOCUMENTS

| | | |
|---|---|---|
| CN | 104906117 A | 9/2015 |
| WO | WO-03023065 A1 | 3/2003 |
| WO | WO-03050290 A2 | 6/2003 |
| WO | WO-2006113590 A2 | 10/2006 |
| WO | WO-2009100029 A1 | 8/2009 |
| WO | WO-2011009104 A1 | 1/2011 |
| WO | WO-2012054975 A1 | 5/2012 |

(Continued)

OTHER PUBLICATIONS

Daudoux P, Journal of Virology, 1998, vol. 72, pp. 8636-8643.*
Abravaya, et al., Detection of point mutations with a modified ligase chain reaction (Gap-LCR), Nucleic Acids Research, Feb. 1995, pp. 675-682.
Al-Nedawi, et al., Intercellular transfer of the oncogenic receptor EGFRvIII by microvesicles derived from tumour cells, Nat Cell Bioi., May 2008, pp. 619-624.
Attostar Q-Beta Bacteriophage as an RNA Extraction and RT-PCR Control (online), Attostar LLC, 2007, 9 pages.
Balzar, et al., The biology of the 17-1A antigen (Ep-CAM), J Mol Med., Oct. 1999, pp. 699-712.

(Continued)

*Primary Examiner* — Bao Q Li
(74) *Attorney, Agent, or Firm* — Casimir Jones, S.C.; Peter J. Schlueter

(57) ABSTRACT

The present disclosure provides compositions, methods and kits for internal controls of microvesicle isolations. The compositions, methods and kits can comprise enveloped viruses, including, but not limited to, inactive mouse hepatitis virus (MHV).

19 Claims, 20 Drawing Sheets

(56) References Cited

FOREIGN PATENT DOCUMENTS

| WO | WO-2014036391 A1 | 3/2014 |
|----|------------------|--------|
| WO | WO-2014107571 A1 | 7/2014 |
| WO | WO-2015021158 A1 | 2/2015 |
| WO | WO-2016007755 A1 | 1/2016 |
| WO | WO-2017197399 A1 | 11/2017 |
| WO | WO-2018076018 A1 | 4/2018 |
| WO | WO-2020106853 A1 | 5/2020 |

OTHER PUBLICATIONS

Bossi, et al., Molecularly imprinted polymers for the recognition of proteins: The state of the art, Biosensors and Bioelectronics, Jan. 2007, pp. 1131-1137.
Cheruvanky, et al., Rapid isolation of urinary exosomal biomarkers using a nanomembrane ultrafiltration concentrator, Am J Physiol Renal Physiol., May 2007, pp. F1657-F1661.
Cotton, et al., Reactivity of cytosine and thymine in single-base-pair mismatches with hydroxylamine and osmium tetroxide and its application to the study of mutations, Proc Natl Acad Sci., Jun. 1988, pp. 4397-4401.
Fischer, et al., [11] Two-dimensional electrophoretic separation of restriction enzyme fragments of DNA, Methods in Enzymology, Jan. 1979, pp. 183-191.
Fischer, et al., Length-independent separation of DNA restriction fragments in two-dimensional gel electrophoresis, Cell, Jan. 1979, pp. 191-200.
Furnari, et al., Malignant astrocytic glioma: genetics, biology, and paths to treatment, Genes & Developmet, Nov. 2007, pp. 2683-2710.
Geiss, et al. Nature Biotechnology, Direct multiplexed measurement of gene expression with color-coded probe pairs, Mar. 2008, pp. 317-325.
Guatelli, et al., Isothermal, in vitro amplification of nucleic acids by a multienzyme reaction modeled after retroviral replication, Proc Natl Acad Sci USA, Mar. 1990, pp. 1874-1878.
Hahn, Molecular biology of double-minute chromosomes, Bioessays, Jul. 1993, pp. 477-484.
Jiang, et al., Synthetic spike-in standards for RNA-seq experiments, Genome Research, Sep. 2011, pp. 1543-1551.
Johnson, et al., Surface-immobilized peptide aptamers as probe molecules for protein detection, Anal Chem., Feb. 2008, pp. 978-983.
Kan, et al., Antenatal diagnosis of sickle-cell anaemia by DNA analysis of amniotic-fluid cells, The Lancet, Oct. 1978, pp. 910-912.
Kan, et al., Polymorphism of DNA sequence adjacent to human ß-globin structural gene: relationship to sickle mutation, PNAS, Nov. 1978, pp. 5631-5635.
Keller, et al., CD24 is a marker of exosomes secreted into urine and amniotic fluid, Kidney Int., Nov. 2007, pp. 1095-1102.
Konoshenko, et al., Isolation of Extracellular Vesicles: General Methodologies and Latest Trends, BioMed Research International, Oct. 2018, 27 pages.
Kwoh, et al., Transcription-based amplification system and detection of amplified human immunodeficiency virus type 1 with a bead-based sandwich hybridization format, Proc Natl Acad Sci., Feb. 1989, pp. 1173-1177.
Landegren, et al., A ligase-mediated gene detection technique, Science, Aug. 1988, pp. 1077-1080.
Li, et al., BEAMing up for detection and quantification of rare sequence variants, Nat Methods, Feb. 2006, pp. 95-97.
Li, et al., Replacing PCR with COLD-PCR enriches variant DNA sequences and redefines the sensitivity of genetic testing, Nature Medicine, May 2008, pp. 579-584.
Miele, et al., Autocatalytic replication of a recombinant RNA, J Mol. Biol., Dec. 1983, pp. 281-295.
Myers, et al., Detection of single base substitutions by ribonuclease cleavage at mismatches in RNA:DNA duplexes, Science, Dec. 1985, pp. 1242-1246.
Nagrath et al., Isolation of rare circulating tumour cells in cancer patients by microchip technology, Nature, Dec. 2007, pp. 1235-1239.
Nakazawa, et al., UV and skin cancer: specific p53 gene mutation in normal skin as a biologically relevant exposure measurement, Proc Natl Acad Sci., Jan. 1994, pp. 360-364.
Neidler, What are the differences between PCR, RT-PCR, qPCR, and RT-qPCR?, Posted by Sarah Neidler, Mar. 2017, 3 pages.
Orita, et al., Detection of polymorphisms of human DNA by gel electrophoresis as single-strand conformation polymorphisms, Proceedings of the National Academy of Sciences, Apr. 1989, pp. 2766-2770.
Pelloski, et al., Epidermal Growth Factor Receptor Variant III Status Defines Clinically Distinct Subtypes of Glioblastoma, Journal of Clinical Oncology, Jun. 2007, pp. 2288-2294.
Raposo, et al., B lymphocytes secrete antigen-presenting vesicles, Journal of Experimental Medicine, Mar. 1996, pp. 1161-1172.
Steemers, et al., Whole-genome genotyping with the single-base extension assay, Nature Methods, Jan. 2006, pp. 31-33.
Taylor, et al., MicroRNA signatures of tumor-derived exosomes as diagnostic biomarkers of ovarian cancer, Gynecol Oncol., Jul. 2008, pp. 13-21.
Thery, et al., Exosomes: composition, biogenesis and function, Nature reviews immunology, 2002, pp. 569-579.
Velculescu, et al., Serial Analysis of Gene Expression, Science, Oct. 1995, pp. 484-487.
Went, et al., Frequent EpCam protein expression in human carcinomas, Hum Pathol., Jan. 2004, pp. 122-128.
Witwer, et al., Standardization of sample collection, isolation and analysis methods in extracellular vesicle research, J. Extracellular Vesicles, Jan. 2013, 25 pages.

\* cited by examiner

COMPOSITIONS AND METHODS FOR INTERNAL CONTROLS OF MICROVESICLE ISOLATIONS

RELATED APPLICATIONS

This application is a U.S. National Stage Application, filed under 35 U.S.C. 371, of International Application No. PCT/US2019/062429, filed on Nov. 20, 2019, which claims priority to, and the benefit of, U.S. Provisional Application No. 62/769,745, filed Nov. 20, 2018, the contents of each of which are incorporated herein by reference in their entirety.

BACKGROUND OF THE INVENTION

Small membrane-bound vesicles shed by cells are described as "microvesicles". Microvesicles may include exosomes, exosome-like particles, prostasomes, dexosomes, texosomes, ectosomes, oncosomes, apoptotic bodies, retrovirus-like particles, and human endogenous retrovirus (HERV) particles. Studies have shown that microvesicles are shed from many different cell types under both normal and pathological conditions (Thery et al., 2002). Importantly, microvesicles have been shown to contain DNA, RNA, and protein. Recent studies have shown that microvesicles contain biomarkers or disease-associated genes that can be detected, therefore, demonstrating the value of microvesicle analysis for aiding in the diagnosis, prognosis, monitoring, or therapy selection for a disease or other medical disease.

Various molecular diagnostic assays are used to detect disease-related biomarkers and provide valuable information for patients, doctors, clinicians, and researchers. Analysis of nucleic acids extracted from microvesicles for diagnostic purposes has wide-ranging implications due to the non-invasive nature in which microvesicles can be easily collected. Use of microvesicle analysis in place of invasive tissue biopsies would positively impact patient welfare, improve the ability to conduct longitudinal disease monitoring, and improve the ability to obtain expression profiles even when tissue cells are not easily accessible (e.g., in ovarian or brain cancer patients). Thus, there is a need in the art for additional compositions and methods to ensure the consistency, reliability, and practicality of diagnostic microvesicle analysis for use in the clinical field is needed. Without proper internal controls, the results of analyses of nucleic acid extracted from microvesicles could be inconsistent and therefore impractical for clinical diagnosis. The present disclosure addresses these needs.

SUMMARY OF THE INVENTION

The present disclosure provides a method comprising: (a) adding a known quantity of control particles comprising at least one control nucleic acid to a biological sample; (b) isolating microvesicles and the control particles from the biological sample; (c) extracting nucleic acids from the microvesicles and the control particles; (d) assaying the amount of the at least one control nucleic acid recovered, thereby determining the amount of control particles recovered; (e) determining that the amount of control particles calculated in step (d) is within a predetermined range of values; and (f) subjecting the nucleic acids from step (c) to further analysis if the amount of control particle calculated in step (d) is within the predetermine range of values.

The present disclosure provides a method comprising: (a) adding a known quantity of control particles comprising at least one control nucleic acid to a biological sample; (b) isolating cell-free DNA, microvesicles and the control particles from the biological sample; (c) extracting nucleic acids from the microvesicles and the control particles; (d) assaying the amount of the at least one control nucleic acid recovered, thereby determining the amount of control particles recovered; (e) determining that the amount of control particles calculated in step (d) is within a predetermined range of values; and (f) subjecting the nucleic acids from step (c) and the cell-free DNA from step (b) to further analysis if the amount of control particle calculated in step (d) is within the predetermine range of values.

The present disclosure provides a method comprising: (a) isolating microvesicles from a biological sample; (b) adding a known quantity of control particles comprising at least one control nucleic acid to the isolated microvesicles; (c) extracting nucleic acids from the isolated microvesicles and the control particles; (d) assaying the amount of the at least one control nucleic acid recovered, thereby determining the amount of control particles recovered; (e) determining that the amount of control particles calculated in step (d) is within a predetermined range of values; and (f) subjecting the nucleic acids from step (c) to further analysis if the amount of control particle calculated in step (d) is within the predetermine range of values.

The present disclosure provides a method comprising: (a) isolating cell-free DNA and microvesicles from a biological sample; (b) adding a known quantity of control particles comprising at least one control nucleic acid to the isolated cell-free DNA and microvesicles; (c) extracting nucleic acids from the isolated microvesicles and the control particles; (d) assaying the amount of the at least one control nucleic acid recovered, thereby determining the amount of control particles recovered; (e) determining that the amount of control particles calculated in step (d) is within a predetermined range of values; and (f) subjecting the nucleic acids from step (c) and the cell-free DNA from step (a) to further analysis if the amount of control particle calculated in step (d) is within the predetermine range of values.

The present disclosure provides a method comprising: (a) adding a known quantity of control particles comprising at least one control nucleic acid and/or at least one control protein to a biological sample, wherein the control particles comprise an enveloped virus; (b) isolating microvesicles and the control particles from the biological sample; (c) extracting nucleic acids and/or protein from the microvesicles and the control particles; (d) assaying the amount of the at least one control nucleic acid and/or at least one control protein recovered, thereby determining the amount of control particles recovered; (e) determining that the amount of control particles calculated in step (d) is within a predetermined range of values; and (f) subjecting the nucleic acids and/or protein from step (c) to further analysis if the amount of control particle calculated in step (d) is within the predetermine range of values.

The present disclosure provides a method comprising: (a) isolating microvesicles from a biological sample; (b) adding a known quantity of control particles comprising at least one control nucleic acid and/or at least one control protein to the isolated microvesicles, wherein the control particles comprise an enveloped virus; (c) extracting nucleic acids and/or protein from the isolated microvesicles and the control particles; (d) assaying the amount of the at least one control nucleic acid and/or at least one control protein recovered, thereby determining the amount of control particles recovered; (e) determining that the amount of control particles calculated in step (d) is within a predetermined range of values; and (f) subjecting the nucleic acids and/or protein from step (c) to further analysis if the amount of control particle calculated in step (d) is within the predetermine range of values.

The present disclosure provides a method comprising: (a) adding a known quantity of control particles comprising at least one control nucleic acid and/or at least one control protein to a biological sample, wherein the control particles comprise an enveloped virus; (b) isolating cell-free DNA, microvesicles and the control particles from the biological sample; (c) extracting nucleic acids and/or protein from the microvesicles and the control particles; (d) assaying the amount of the at least one control nucleic acid and/or at least one control protein recovered, thereby determining the amount of control particles recovered; (e) determining that the amount of control particles calculated in step (d) is within a predetermined range of values; and (f) subjecting the nucleic acids and/or protein from step (c) and the cell-free DNA from step (b) to further analysis if the amount of control particle calculated in step (d) is within the predetermine range of values.

The present disclosure provides a method comprising: (a) isolating cell-free DNA and microvesicles from a biological sample; (b) adding a known quantity of control particles comprising at least one control nucleic acid and/or at least one control protein to the isolated microvesicles, wherein the control particles comprise an enveloped virus; (c) extracting nucleic acids and/or protein from the isolated microvesicles and the control particles; (d) assaying the amount of the at least one control nucleic acid and/or at least one control protein recovered, thereby determining the amount of control particles recovered; (e) determining that the amount of control particles calculated in step (d) is within a predetermined range of values; and (f) subjecting the nucleic acids and/or protein from step (c) and the cell-free DNA from step (b) to further analysis if the amount of control particle calculated in step (d) is within the predetermine range of values.

The present disclosure provides a method comprising: (a) adding a known quantity of control particles comprising at least one control protein to a biological sample, wherein the control particles comprise an enveloped virus; (b) isolating microvesicles and the control particles from the biological sample; (c) extracting protein from the microvesicles and the control particles; (d) assaying the amount of the at least one control protein recovered, thereby determining the amount of control particles recovered; (e) determining that the amount of control particles calculated in step (d) is within a predetermined range of values; and (f) subjecting the protein from step (c) to further analysis if the amount of control particle calculated in step (d) is within the predetermine range of values.

The present disclosure provides a method comprising: (a) isolating microvesicles from a biological sample; (b) adding a known quantity of control particles comprising at least at least one control protein to the isolated microvesicles, wherein the control particles comprise an enveloped virus; (c) extracting protein from the isolated microvesicles and the control particles; (d) assaying the amount of the at least one control protein recovered, thereby determining the amount of control particles recovered; (e) determining that the amount of control particles calculated in step (d) is within a predetermined range of values; and (f) subjecting the protein from step (c) to further analysis if the amount of control particle calculated in step (d) is within the predetermine range of values.

The present disclosure provides a method comprising: (a) adding a known quantity of control particles comprising at least one control protein to a biological sample, wherein the control particles comprise an enveloped virus; (b) isolating cell-free DNA, microvesicles and the control particles from the biological sample; (c) extracting protein from the microvesicles and the control particles; (d) assaying the amount of the at least one control protein recovered, thereby determining the amount of control particles recovered; (e) determining that the amount of control particles calculated in step (d) is within a predetermined range of values; and (f) subjecting the protein from step (c) and the cell-free DNA from step (b) to further analysis if the amount of control particle calculated in step (d) is within the predetermine range of values.

The present disclosure provides a method comprising: (a) isolating cell-free DNA and microvesicles from a biological sample; (b) adding a known quantity of control particles comprising at least one control protein to the isolated microvesicles, wherein the control particles comprise an enveloped virus; (c) extracting protein from the isolated microvesicles and the control particles; (d) assaying the amount of the at least one control protein recovered, thereby determining the amount of control particles recovered; (e) determining that the amount of control particles calculated in step (d) is within a predetermined range of values; and (f) subjecting the protein from step (c) and the cell-free DNA from step (b) to further analysis if the amount of control particle calculated in step (d) is within the predetermine range of values.

The control particle can comprise an enveloped virus. The enveloped virus can be a non-human animal enveloped virus. The non-human animal enveloped virus can be an inactivated non-human animal enveloped virus. The enveloped virus can be a human enveloped virus. The human enveloped virus can be an inactivated human enveloped virus. The inactivated non-human animal enveloped virus can be mouse hepatitis virus (MHV), or bovine viral diarrhea virus (BVDV), or transmissible gastroenteritis coronavirus (TGE V).

The biological sample can be a bodily fluid sample. The bodily fluid sample can be urine, blood, cerebrospinal fluid or serum.

The at least one control nucleic acid can comprise RNA.

The nucleic acids from step (c) of the preceding methods can comprise RNA. The nucleic acids from step (c) of the preceding methods can comprise DNA. The nucleic acids from step (c) of the preceding methods can comprise RNA and DNA.

Assaying the amount of the at least one control nucleic acid recovered in step (d) of the preceding methods can comprise assaying the expression level or copy number of the control nucleic acid. Assaying the expression level or copy number of the control nucleic acid can comprise reverse transcribing the control nucleic acid. Assaying the expression level or copy number of the control nucleic acid can comprise quantitative PCR (qPCR).

Step (f) of the preceding methods can comprise determining the presence, absence or level of at least one biomarker associated with a disease or medical condition for diagnosing, prognosing, or monitoring the disease or medical condition. Determining the presence, absence or level of at least one biomarker associated with a disease or medical condition for diagnosing, prognosing, or monitoring the disease or medical condition can comprise reverse transcription. Determining the presence, absence or level of at least one biomarker associated with a disease or medical condition for diagnosing, prognosing, or monitoring the disease or medical condition can comprise quantitative PCR. Quantitative PCR can comprise reverse transcription quantitative PCR (RT-qPCR).

Any of the above aspects can be combined with any other aspect.

Unless otherwise defined, all technical and scientific terms used herein have the same meaning as commonly understood by one of ordinary skill in the art to which this disclosure belongs. In the Specification, the singular forms also include the plural unless the context clearly dictates otherwise; as examples, the terms "a," "an," and "the" are understood to be singular or plural and the term "or" is understood to be inclusive. By way of example, "an element" means one or more element. Throughout the specification the word "comprising," or variations such as "comprises" or "comprising," will be understood to imply the inclusion of a stated element, integer or step, or group of elements, integers or steps, but not the exclusion of any other element, integer or step, or group of elements, integers or steps. About can be understood as within 10%, 9%, 8%, 7%, 6%, 5%, 4%, 3%, 2%, 1%, 0.5%, 0.1%, 0.05%, or 0.01% of the stated value. Unless otherwise clear from the context, all numerical values provided herein are modified by the term "about."

Although methods and materials similar or equivalent to those described herein can be used in the practice or testing of the present disclosure, suitable methods and materials are described below. All publications, patent applications, patents, and other references mentioned herein are incorporated by reference in their entirety. The references cited herein are not admitted to be prior art to the claimed invention. In the case of conflict, the present Specification, including definitions, will control. In addition, the materials, methods, and examples are illustrative only and are not intended to be limiting. Other features and advantages of the disclosure will be apparent from the following detailed description and claim.

BRIEF DESCRIPTION OF THE DRAWINGS

The above and further features will be more clearly appreciated from the following detailed description when taken in conjunction with the accompanying drawings.

DETAILED DESCRIPTION OF THE INVENTION

Figure 1:
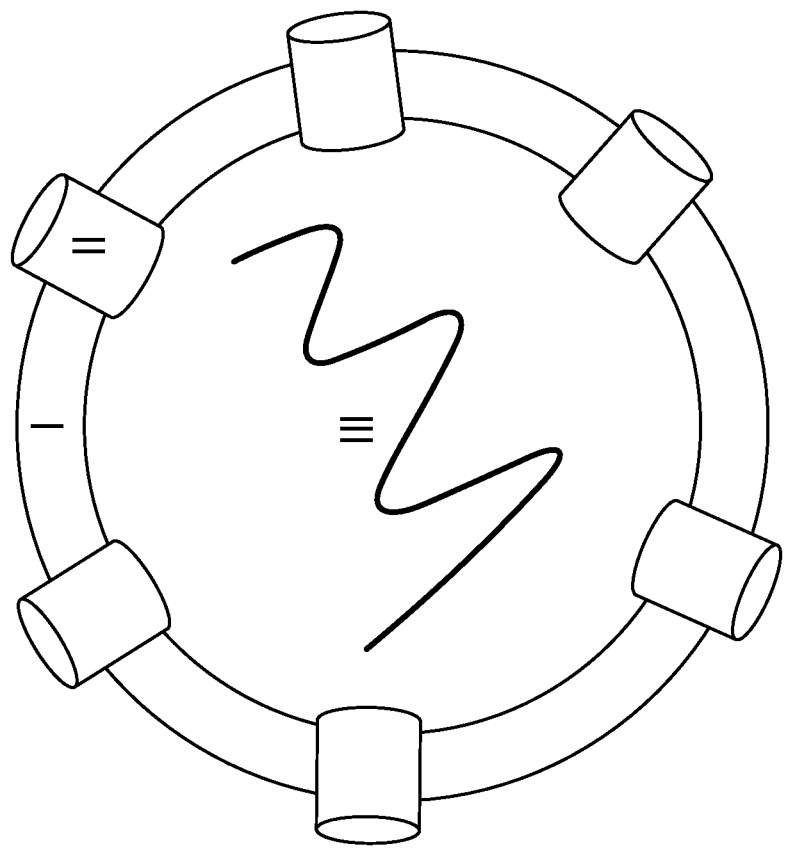
FIG. 1 is a schematic diagram of an enveloped virus.
Figure 2:
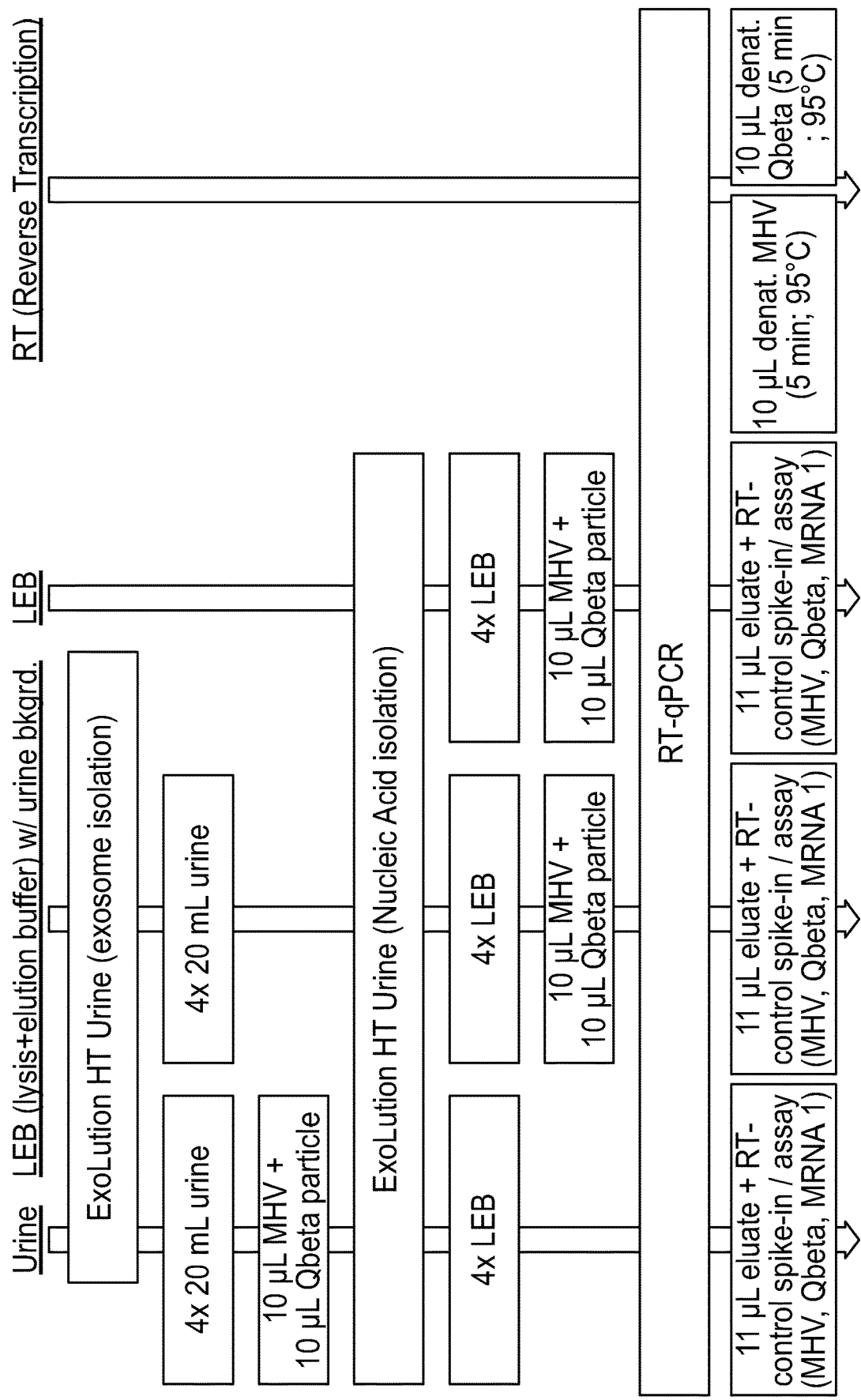
FIG. 2 is a schematic overview of isolation experiments using MHV particles and urine samples.
Figure 3:
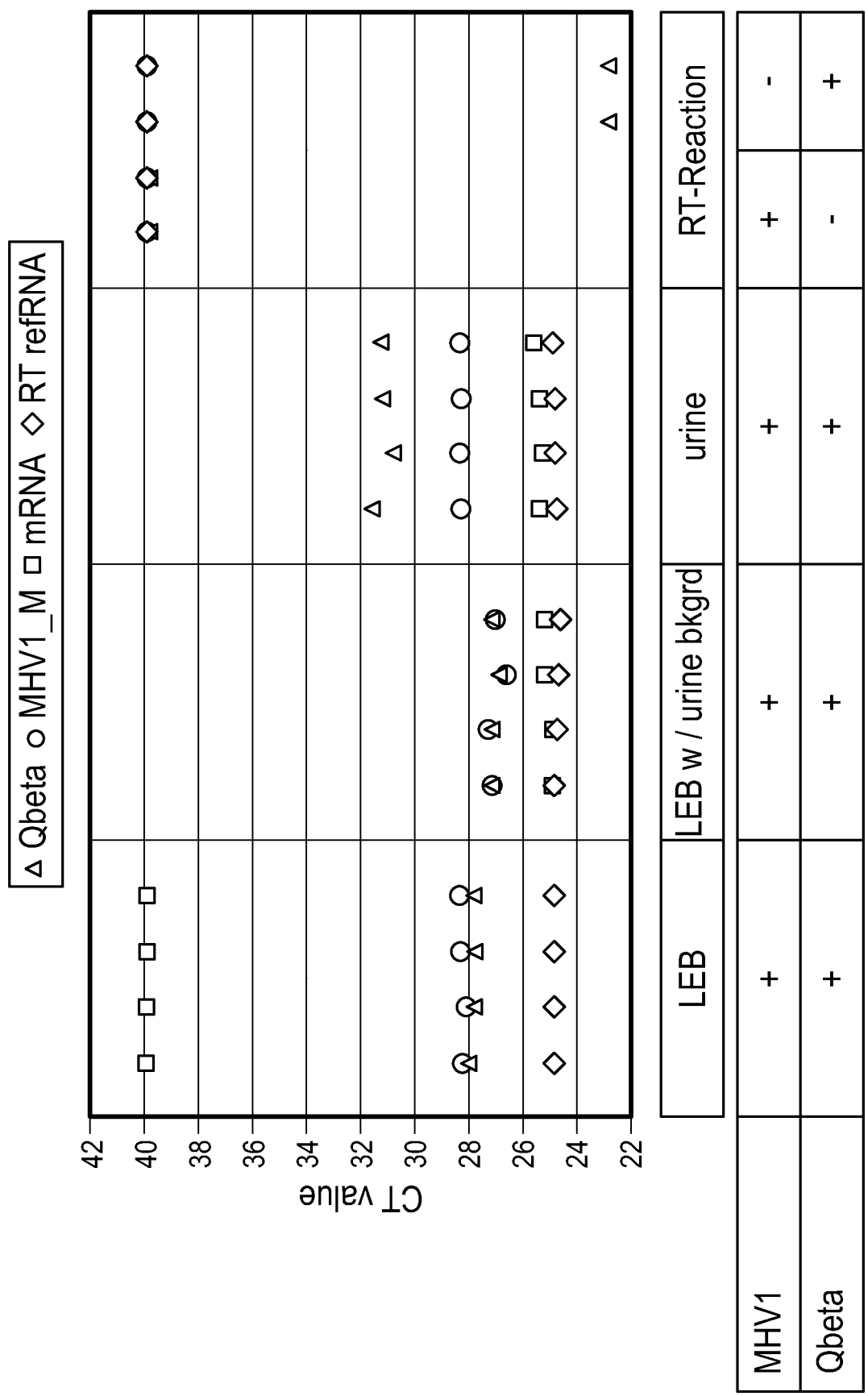
FIG. 3 is a graph showing RT-qPCR results from isolation experiments using MHV particles and urine samples.
Figure 4:
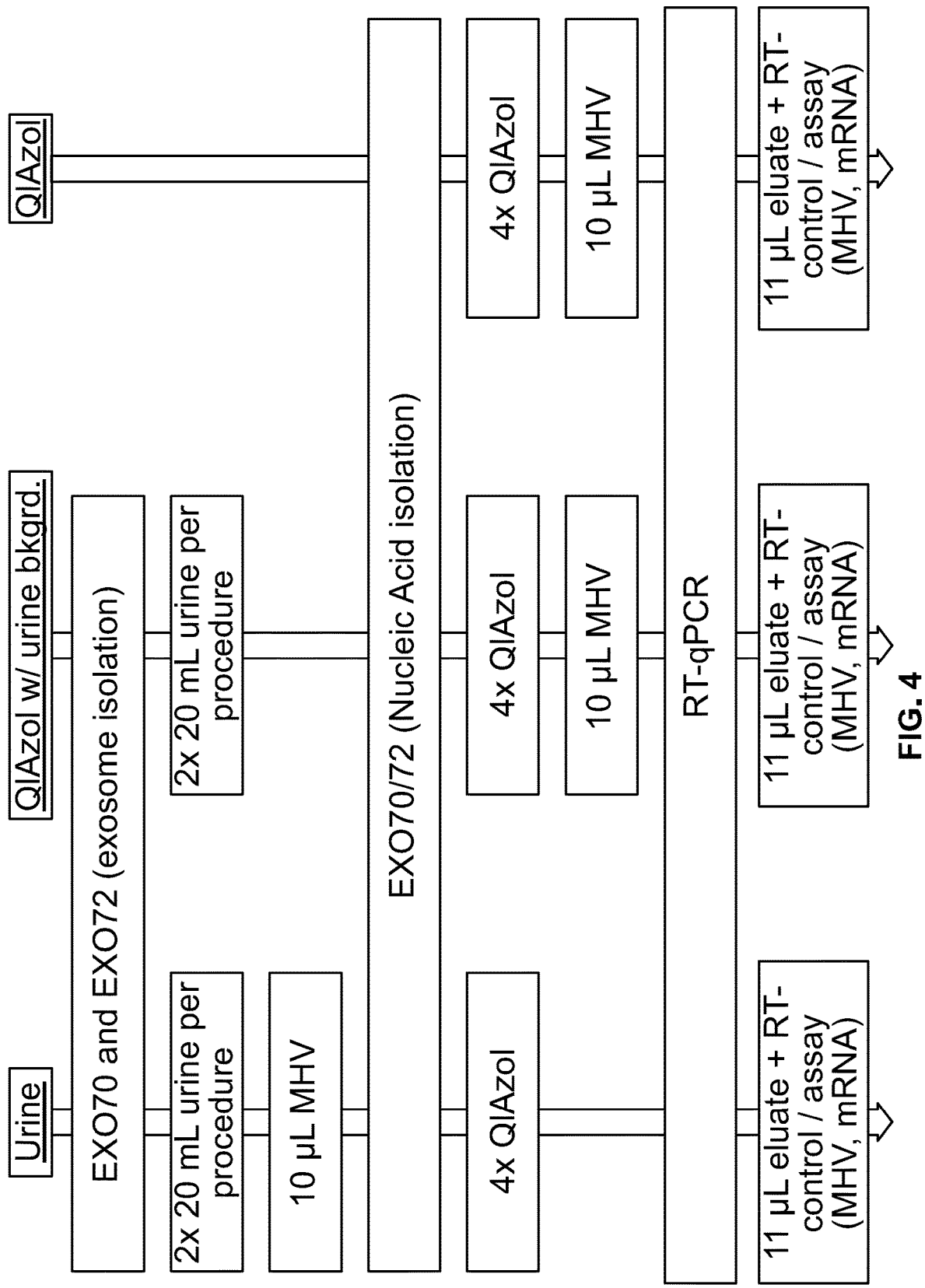
FIG. 4 is a schematic overview of isolation experiments using MHV particles and urine samples.
Figure 5:
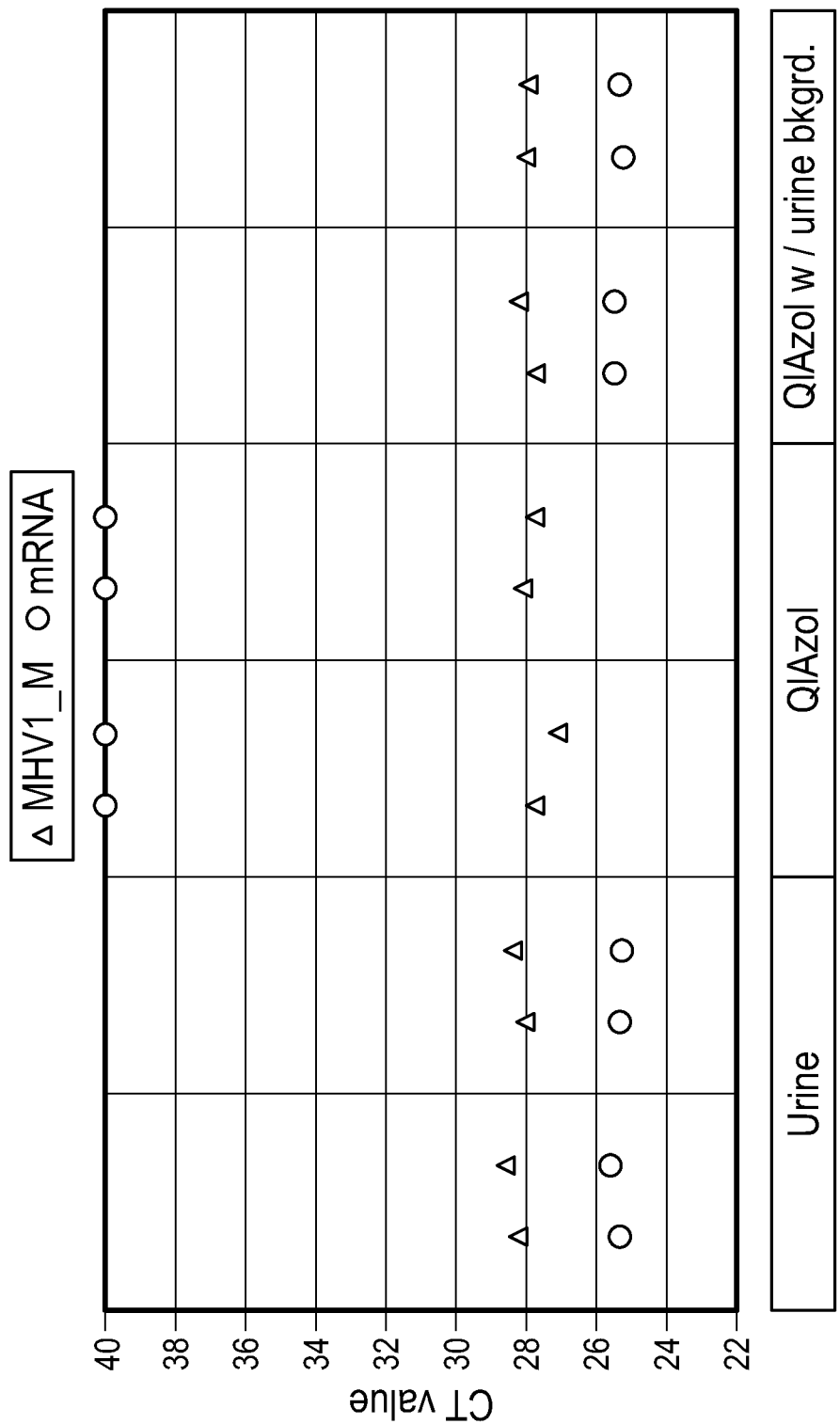
FIG. 5 is a graph showing RT-qPCR results from isolation experiments using MHV particles and urine samples.

Microvesicles have been previously shown to be valuable diagnostic and prognostic tools. All membrane vesicles shed by cells <0.8 µm in diameter are referred to herein collectively as microvesicles. This may include exosomes, exosome-like particles, prostasomes, dexosomes, texosomes, ectosomes, oncosomes, apoptotic bodies, retrovirus-like particles, and human endogenous retrovirus (HERV) particles. Microvesicles from various cell sources have been extensively studied with respect to protein and lipid content. Microvesicles are also known to contain nucleic acids, including various DNA and RNA types such as mRNA (messenger RNA), miRNA (micro RNA), tRNA (transfer RNA), piRNA (piwi-interacting RNA), snRNA (small nuclear RNA), snoRNA (small nucleolar RNA), and rRNA (ribosomal RNA), various classes of long non-coding RNA, including long intergenic non-coding RNA (lincRNA). Recent studies reveal that nucleic acids within microvesicles have a role as biomarkers.

Microvesicles can be isolated from liquid biopsy samples from a subject, involving biofluids such as whole blood, serum, plasma, urine, and cerebrospinal fluid (CSF). The nucleic acids contained within the microvesicles can subsequently be extracted. The extracted nucleic acids, e.g., exosomal RNA, also referred to herein as "exoRNA," can be further analyzed based on detection of a biomarker or a combination of biomarkers. The analysis can be used to generate a clinical assessment that diagnoses a subject with a disease, predicts the disease outcome of the subject, stratifies the subject within a larger population of subjects, predicts whether the subject will respond to a particular therapy, or determines if a subject is responding to an administered therapy.

For example, an initial study demonstrated that glioblastoma-derived microvesicles could be isolated from the serum of glioblastoma patients. Importantly, these microvesicles contain mRNA associated with the tumor cells. The nucleic acids within these microvesicles can be used as valuable biomarkers for tumor diagnosis, characterization and prognosis. The nucleic acids within the microvesicles can be used to monitor tumor progression over time by analyzing if other mutations are acquired over time or over the course of treatment. In addition, levels of disease-associated genes can also be determined and compiled into a genetic expression profile which can be compared to reference profiles to diagnose or prognose a disease or monitor the progression of a disease or therapeutic regimen.

Internal controls are often used during isolation and/or extraction processes to determine the efficiency of the process, or the quality of the resulting isolation or extraction. Internal controls for isolation and/or extraction processes can include the addition of a control particle to a sample to control for the efficiency, quality and/or purity of the isolation and/or extraction process.

The present disclosure provides compositions, methods and kits comprising a control particle as an internal control for methods of isolating microvesicles and/or extracting nucleic acids from microvesicles. The quality or purity of the microvesicle fraction or the extracted microvesicle nucleic acids can directly affect the efficiency and sensitivity of the subsequent processes for assaying biomarkers for disease diagnosis, characterization, and prognosis. Given the importance of accurate and sensitive diagnostic tests in the clinical field, the compositions, methods and kits described herein are used to evaluate the quality of microvesicle isolation and microvesicle nucleic acid extraction to increase the reliability and sensitivity of microvesicle-based assays and diagnostics. The compositions, methods and kits described herein can be used to identify microvesicle nucleic acid extractions that are suitable for further analysis of disease-associated biomarkers for diagnostic, prognostic, and therapeutic applications. The compositions, methods and kits described herein can be used to identify microvesicle nucleic acid extractions that are unsuitable for further analysis of disease-associated biomarkers, or would yield inaccurate results, in diagnostic, prognostic, and therapeutic applications. Thus, the compositions, methods and kits described herein can be used to distinguish high quality microvesicle isolations and nucleic acid extractions from low quality microvesicle isolations and nucleic acid extractions, such that the high quality microvesicle isolations or nucleic acid extractions yield accurate results from subsequent analysis steps (i.e., biomarker analysis).

In some aspects, the compositions, methods and kits of the present disclosure comprise control particles, such as mouse hepatitis virus (MHV), that are similar in size to microvesicles to control for the efficiency, quality or purity of the microvesicle isolation and the nucleic acids extracted from the isolated microvesicles.

The present disclosure provides a method comprising: (a) adding a known quantity of control particles comprising at least one control nucleic acid to a biological sample; (b) isolating microvesicles and the control particles from the biological sample; (c) extracting nucleic acids from the microvesicles and the control particles; (d) assaying the amount of the at least one control nucleic acid recovered, thereby determining the amount of control particles recovered; (e) determining that the amount of control particles calculated in step (d) is within a predetermined range of values; and (f) subjecting the nucleic acids from step (c) to further analysis if the amount of control particle calculated in step (d) is within the predetermine range of values.

The present disclosure also provides a method comprising: (a) adding a known quantity of control particles comprising at least one control nucleic acid to a biological sample, wherein the control particles are mouse hepatitis virus (MHV) particles; (b) isolating microvesicles and the control particles from the biological sample; (c) extracting nucleic acids from the microvesicles and the control particles; (d) assaying the amount of the at least one control nucleic acid recovered, thereby determining the amount of control particles recovered; (e) determining that the amount of control particles calculated in step (d) is within a predetermined range of values; and (f) subjecting the nucleic acids from step (c) to further analysis if the amount of control particle calculated in step (d) is within the predetermine range of values.

The present disclosure provides a method comprising: (a) isolating microvesicles from a biological sample; (b) adding a known quantity of control particles comprising at least one control nucleic acid to the isolated microvesicles; (c) extracting nucleic acids from the isolated microvesicles and the control particles; (d) assaying the amount of the at least one control nucleic acid recovered, thereby determining the amount of control particles recovered; (e) determining that the amount of control particles calculated in step (d) is within a predetermined range of values; and (f) subjecting the nucleic acids from step (c) to further analysis if the amount of control particle calculated in step (d) is within the predetermine range of values.

The present disclosure also provides a method comprising: (a) isolating microvesicles from a biological sample; (b) adding a known quantity of control particles comprising at least one control nucleic acid to the isolated microvesicles, wherein the control particles are mouse hepatitis virus (MHV) particles; (c) extracting nucleic acids from the isolated microvesicles and the control particles; (d) assaying the amount of the at least one control nucleic acid recovered, thereby determining the amount of control particles recovered; (e) determining that the amount of control particles calculated in step (d) is within a predetermined range of values; and (f) subjecting the nucleic acids from step (c) to further analysis if the amount of control particle calculated in step (d) is within the predetermine range of values.

The present disclosure provides a method comprising: (a) adding a known quantity of control particles comprising at least one control nucleic acid to a biological sample; (b) isolating microvesicles and the control particles from the biological sample; (c) extracting nucleic acids from the microvesicles and the control particles; (d) assaying the amount of the at least one control nucleic acid recovered, thereby determining the amount of control particles recovered; (e) determining that the amount of control particles calculated in step (d) is within a predetermined range of values; and (f) subjecting the nucleic acids from step (c) to further analysis if the amount of control particle calculated in step (d) is within the predetermine range of values.

The present disclosure provides a method comprising: (a) adding a known quantity of control particles comprising at least one control nucleic acid to a biological sample; (b) isolating cell-free DNA, microvesicles and the control particles from the biological sample; (c) extracting nucleic acids from the microvesicles and the control particles; (d) assaying the amount of the at least one control nucleic acid recovered, thereby determining the amount of control particles recovered; (e) determining that the amount of control particles calculated in step (d) is within a predetermined range of values; and (f) subjecting the nucleic acids from step (c) and the cell-free DNA from step (b) to further analysis if the amount of control particle calculated in step (d) is within the predetermine range of values.

The present disclosure provides a method comprising: (a) isolating microvesicles from a biological sample; (b) adding a known quantity of control particles comprising at least one control nucleic acid to the isolated microvesicles; (c) extracting nucleic acids from the isolated microvesicles and the control particles; (d) assaying the amount of the at least one control nucleic acid recovered, thereby determining the amount of control particles recovered; (e) determining that the amount of control particles calculated in step (d) is within a predetermined range of values; and (f) subjecting the nucleic acids from step (c) to further analysis if the amount of control particle calculated in step (d) is within the predetermine range of values.

The present disclosure provides a method comprising: (a) isolating cell-free DNA and microvesicles from a biological sample; (b) adding a known quantity of control particles comprising at least one control nucleic acid to the isolated cell-free DNA and microvesicles; (c) extracting nucleic acids from the isolated microvesicles and the control particles; (d) assaying the amount of the at least one control nucleic acid recovered, thereby determining the amount of control particles recovered; (e) determining that the amount of control particles calculated in step (d) is within a predetermined range of values; and (f) subjecting the nucleic acids from step (c) and the cell-free DNA from step (a) to further analysis if the amount of control particle calculated in step (d) is within the predetermine range of values.

The present disclosure provides a method comprising: (a) adding a known quantity of control particles comprising at least one control nucleic acid and/or at least one control protein to a biological sample, wherein the control particles comprise an enveloped virus; (b) isolating microvesicles and the control particles from the biological sample; (c) extracting nucleic acids and/or protein from the microvesicles and the control particles; (d) assaying the amount of the at least one control nucleic acid and/or at least one control protein recovered, thereby determining the amount of control particles recovered; (e) determining that the amount of control particles calculated in step (d) is within a predetermined range of values; and (f) subjecting the nucleic acids and/or protein from step (c) to further analysis if the amount of control particle calculated in step (d) is within the predetermine range of values.

The present disclosure provides a method comprising: (a) isolating microvesicles from a biological sample; (b) adding a known quantity of control particles comprising at least one control nucleic acid and/or at least one control protein to the isolated microvesicles, wherein the control particles comprise an enveloped virus; (c) extracting nucleic acids and/or protein from the isolated microvesicles and the control particles; (d) assaying the amount of the at least one control nucleic acid and/or at least one control protein recovered, thereby determining the amount of control particles recovered; (e) determining that the amount of control particles calculated in step (d) is within a predetermined range of values; and (f) subjecting the nucleic acids and/or protein from step (c) to further analysis if the amount of control particle calculated in step (d) is within the predetermine range of values.

The present disclosure provides a method comprising: (a) adding a known quantity of control particles comprising at least one control nucleic acid and/or at least one control protein to a biological sample, wherein the control particles comprise an enveloped virus; (b) isolating cell-free DNA, microvesicles and the control particles from the biological sample; (c) extracting nucleic acids and/or protein from the microvesicles and the control particles; (d) assaying the amount of the at least one control nucleic acid and/or at least one control protein recovered, thereby determining the amount of control particles recovered; (e) determining that the amount of control particles calculated in step (d) is within a predetermined range of values; and (f) subjecting the nucleic acids and/or protein from step (c) and the cell-free DNA from step (b) to further analysis if the amount of control particle calculated in step (d) is within the predetermine range of values.

The present disclosure provides a method comprising: (a) isolating cell-free DNA and microvesicles from a biological sample; (b) adding a known quantity of control particles comprising at least one control nucleic acid and/or at least one control protein to the isolated microvesicles, wherein the control particles comprise an enveloped virus; (c) extracting nucleic acids and/or protein from the isolated microvesicles and the control particles; (d) assaying the amount of the at least one control nucleic acid and/or at least one control protein recovered, thereby determining the amount of control particles recovered; (e) determining that the amount of control particles calculated in step (d) is within a predetermined range of values; and (f) subjecting the nucleic acids and/or protein from step (c) and the cell-free DNA from step (b) to further analysis if the amount of control particle calculated in step (d) is within the predetermine range of values.

The present disclosure provides a method comprising: (a) adding a known quantity of control particles comprising at least one control protein to a biological sample, wherein the control particles comprise an enveloped virus; (b) isolating microvesicles and the control particles from the biological sample; (c) extracting protein from the microvesicles and the control particles; (d) assaying the amount of the at least one control protein recovered, thereby determining the amount of control particles recovered; (e) determining that the amount of control particles calculated in step (d) is within a predetermined range of values; and (f) subjecting the protein from step (c) to further analysis if the amount of control particle calculated in step (d) is within the predetermine range of values.

The present disclosure provides a method comprising: (a) isolating microvesicles from a biological sample; (b) adding a known quantity of control particles comprising at least at least one control protein to the isolated microvesicles, wherein the control particles comprise an enveloped virus; (c) extracting protein from the isolated microvesicles and the control particles; (d) assaying the amount of the at least one control protein recovered, thereby determining the amount of control particles recovered; (e) determining that the amount of control particles calculated in step (d) is within a predetermined range of values; and (f) subjecting the protein from step (c) to further analysis if the amount of control particle calculated in step (d) is within the predetermine range of values.

The present disclosure provides a method comprising: (a) adding a known quantity of control particles comprising at least one control protein to a biological sample, wherein the control particles comprise an enveloped virus; (b) isolating cell-free DNA, microvesicles and the control particles from the biological sample; (c) extracting protein from the microvesicles and the control particles; (d) assaying the amount of the at least one control protein recovered, thereby determining the amount of control particles recovered; (e) determining that the amount of control particles calculated in step (d) is within a predetermined range of values; and (f) subjecting the protein from step (c) and the cell-free DNA from step (b) to further analysis if the amount of control particle calculated in step (d) is within the predetermine range of values.

The present disclosure provides a method comprising: (a) isolating cell-free DNA and microvesicles from a biological sample; (b) adding a known quantity of control particles comprising at least one control protein to the isolated microvesicles, wherein the control particles comprise an enveloped virus; (c) extracting protein from the isolated microvesicles and the control particles; (d) assaying the amount of the at least one control protein recovered, thereby determining the amount of control particles recovered; (e) determining that the amount of control particles calculated in step (d) is within a predetermined range of values; and (f) subjecting the protein from step (c) and the cell-free DNA from step (b) to further analysis if the amount of control particle calculated in step (d) is within the predetermine range of values.

Control Particles

The present disclosure provides use of control particles as an internal control to isolate microvesicles and/or extract nucleic acids from the isolated microvesicles. In some aspects, the use of control particles aid in the evaluation of the efficiency and/or quality of microvesicle isolation and/or nucleic acid extraction from the isolated microvesicles.

Control particles, as used herein, collectively refer to particles of the size range of microvesicles (e.g., less than 0.8 µm in diameter) that are added at some point during the microvesicle isolation process (e.g., prior to microvesicle isolation or prior to nucleic acid extraction). Control particles can contain control nucleic acids, such as DNA or RNA. Specifically, the control nucleic acids contain target sequences or genes that are assayed or measured to determine the amount of recovered control particles after the isolation or extraction process to distinguish high quality microvesicle isolations or nucleic acid extractions. Control particles can contain at least one control protein. Specifically, control proteins are assayed or measured to determine the amount of recovered control particles after the isolation or extraction process to distinguish high quality microvesicle isolations, nucleic acid extractions and protein extractions.

In some aspects, a control particle is of similar size to the size of microvesicles of interest. Control particles can be selected to use as a control based on the size range of the microvesicles to be analyzed, such that a control particle is a similar size to the microvesicle. For example, a control particle is less than 2%, 5%, 10%, 15%, 20% or 50% larger than the microvesicles to be isolated. For example, a control particle is less than 2%, 5%, 10%, 15%, 20% or 50% smaller than the microvesicles to be isolated. Given the size similarity to microvesicles, a control particles can be co-purified with the microvesicles if added to the biological sample prior to the microvesicle purification step.

In some aspects, a control particle is a virus particle. Virus particles, as used herein, collectively refers to viruses, virions, and virus-like particles. Virus particles may be naturally-occurring, modified, recombinant, or engineered.

A virus is a small infectious agent that depends on the host cell that it infects to reproduce. Viruses can infect all types of organisms, from animals and plants to bacteria and archaea. Virus particles comprise: a viral genome; a protein coat that protects the genome called the capsid; and a lipid membrane called the viral envelope that surrounds the capsid. Viruses have either DNA or RNA genomes and are called a DNA virus or a RNA virus, respectively. The vast majority of viruses have RNA genomes. The viral genome can be single-stranded or double-stranded, and linear or circular. Viral genome size varies; the smallest is 2 kilobases and encodes only 2 proteins, while the largest viral genome is over 1.2 megabases and encodes over 1,000 proteins. In general, RNA viruses have smaller genome sizes than DNA viruses due to a higher error-rate when replicating. RNA viruses also have a maximum upper size limit. Virus particles can range in size from 0.005 to 0.3 µm (or 5-300 nm).

In some aspects, a control particle can be an enveloped virus. An enveloped virus is a virus that comprises a lipid bilayer that encapsulates a nucleic acid cargo, as shown in FIG. 1.

In some aspects, a control particle can be a non-human animal enveloped virus. A non-human animal enveloped virus can activated or inactivated.

In some aspects, a control particle can be a human enveloped virus. A human enveloped virus can be activated or inactivated.

In some aspects, a control particle is a DNA virus. DNA viruses of the present disclosure include, but are not limited to, members of the following DNA virus families: Adenoviridae, Papillomaviridae, Parvoviridae, Herpesviridae, Poxviridae, Hepadnaviridae, Polyomaviridae, and Anelloviridae.

In some aspects, a control particle is a RNA virus. The RNA viruses of the present disclosure include, but are not limited to, the members of the following RNA virus families: Picornaviridae, Flaviviridae, Filoviridae, Orthomyxoviridae, Paramyxoviridae Togaviridae, Rhabdoviridae, and Retroviridae. An RNA virus can be, but is not limited to, poliovirus, enterovirus, coxsackievirus, echovirus, hepatitis A virus, hepatitis C virus, encephalomyocarditis virus (EMCV), foot-and-mouth disease virus (FMDV), Dengue virus, Yellow Fever Virus, West Nile virus, bovine viral diarrhea virus (BVDV), eastern encephalitis, western encephalitis, rubella virus, human immunodeficiency virus, simian immunodeficiency virus (SIV), feline immunodeficiency virus, Marburg virus, Ebola virus, influenza virus, measles virus, mouse hepatitis virus (MHV), bovine viral diarrhea virus (BVDV), transmissible gastroenteritis coronavirus (TGEV) or rabies virus.

In some aspects a control particle is a bacteriophage ("phage"). There are estimated to be at least several hundred thousands of phage species existing in nature. Phages are classified by morphology (e.g., tailed, polyhedral, filamentous, or pleomorphic) and physiology (e.g., linear or circular genome, single or double stranded genome, or no capsid). Bacteriophages are classified into 11 families: caudovirales, myoviridae, siphoviridae, podoviridae, microviridae, corticoviridae, tectiviridae, leviviridae, cystoviridae, inoviridae, and plasmaviridae. The two classes of RNA bacteriophages are leviviridae and cystoviridae. Leviviridae is characterized by single stranded RNA genomes and cystoviridae is characterized by double-stranded RNA genomes.

In some aspects, a control particle is a DNA bacteriophage, where the genome is DNA. For example, the bacteriophage is an Ancholeplasma phage, a coliphage, ϕX174, a spiroplasma phage, or a Mac-1 phage.

In a some aspects, a control particle is a RNA bacteriophage. For example, a control particle is selected from the group consisting of Q-beta, MS2, f2, R17, GA, SP, and ϕ6.

In other aspects, a control particle is an engineered or recombinant virus particle, wherein at least one component of the virus particle (e.g., genes or fragments thereof of the genome) is modified, synthesized, or introduced by recombinant DNA or molecular biology techniques known in the art. In other aspects, a control particle contains a genome that is partially or entirely modified, synthesized, or introduced by recombinant techniques. For example, the recombinant virus particle contains a recombinant RNA genome that includes specific nucleotide sequences corresponding to primers for amplification of a particular sequence of the recombinant RNA genome. The use of the same primer set for amplifying the control nucleic acids and the gene of interest eliminates any risk of interference and/or reduces background signal and false priming by the control virus particle primers. Methods for creating a recombinant virus particle are known in the art.

In other aspects, a control particle is an engineered microparticle containing control nucleic acids generated by recombinant DNA methods. The control particle is a microvesicle produced by cells in culture.

Control Nucleic Acids

A control nucleic acid of the present disclosure comprises a control target gene or control target sequence to be detected and/or quantified to determine the amount of control particles recovered in a sample after the microvesicle isolation and nucleic extraction process. The control target gene is measured by nucleic acid amplification techniques, using specific primers that recognize the control target gene. In some aspects, a probe is utilized to detect the amplified control target gene. In some aspects, the control nucleic acid or control target gene is measured by RT-PCR analysis. In some aspects, the control nucleic acid is a nucleic acid that is not endogenously found in the biological sample being tested.

A control particle of the present disclosure can contain at least one control nucleic acid to be detected. A control nucleic acid can be RNA or DNA. A control nucleic acid can be double-stranded or single stranded. Preferably, a control nucleic acid has low complexity. Low complexity regions are defined as regions composed of only a few elements (i.e., coding regions, non-coding regions, and repeats). Control particles with low complexity control nucleic acids are preferred because the low complexity reduces the potential of false priming with a gene of interest in target microvesicles in the amplification analysis step.

Control Proteins

A control protein of the present disclosure can comprise a control polypeptide sequence or a portion of target polypeptide sequence to be detected and/or quantified to determine the amount of control particles recovered in a sample after the microvesicle isolation and nucleic extraction process. A control protein of the present disclosure can be measured using any standard technique in the art, including, but not limited to, Western Blot analysis, SDS-PAGE analysis, mass spectrometry analysis or any combination thereof. In some aspects, a probe is utilized to detect the control protein. The probe can comprise an antibody.

A control particle of the present disclosure can contain at least one control protein be detected. A control protein can be any protein that is present on or in the control particle. For example, a control protein can be a membrane protein or a soluble protein.

Use of Control Particles in Microvesicle Analysis

Detection and quantification of control particles recovered after microvesicle isolation and/or nucleic acid extraction is useful for distinguishing high quality microvesicle preparations and/or nucleic acid preparations from low quality microvesicle preparations and/or nucleic acid preparations. As used herein, "microvesicle preparations" refers to the fraction comprising microvesicles after the isolation process. As used herein, "nucleic acid preparations" refers to the extracted nucleic acids from the isolated microvesicles.

A known quantity or number of control particles is added to the biological sample prior to microvesicle isolation. The control particles are quantified before being added to the sample. The known quantity or copy number of control particles can be determined by methods known in the art including, but not limited to, tissue culture infective dose, plaque forming units, colony forming units, flow cytometry-based methods, and ELISA assays. The known quantity of control particles can be about 1 to about 1,000,000 copies of the control particle. In a non-limiting example, the known quantity can be about 1, 2, 3, 4, 5, 6, 7, 8, 9, 10, 11, 12, 13, 14, 15, 16, 17, 18, 19, 20, 21, 22, 23, 24, 25, 50, 75, 100, 150, 200, 300, 350, 400, 450, 500, 1,000, 5,000, 10,000, 50,000, 100,000, 500,000, 1,000,000, 5,000,000, $1 \times 10^7$, $1 \times 10^8$, $1 \times 10^9$, $1 \times 10^{10}$, $1 \times 10^{11}$, copies of the control particle. In some aspects, the known quantity of control particles is high enough to have a signal that is out of the stochastic range but low enough to be sensitive to potential processing errors and low enough to not disturb downstream analysis.

In some aspects, a known quantity of control particles is added to a biological sample prior to the isolation of a fraction comprising microvesicles. In these aspects, the control particle is present during the microvesicle isolation and nucleic acid extraction steps. Because microvesicles and control particles are similar in size, the microvesicle isolation procedure can also isolate the control particles. Therefore, the recovery of the control particles indicates the recovery of microvesicles, and therefore, high recovery of the control particles indicates high quality of the resulting microvesicle preparation.

In some aspects, a known quantity of control particles is added to a fraction comprising microvesicles that is isolated from a biological sample. In this aspect, a mixture comprising the microvesicles isolated from the biological sample and the control particles is created. Nucleic acids from both the control particle and the microvesicles are extracted in a subsequent extraction step. Therefore, the recovery and/or quality of the control nucleic acids from the control particles indicates the recovery and/or quality of nucleic acids from the microvesicles, and therefore, high quality/quantity of the control nucleic acids indicates high quality/quantity of the resulting nucleic acid preparation comprising microvesicle nucleic acids.

In some aspects, a known quantity of control particles is added to a fraction comprising microvesicles that is isolated from a biological sample. In this aspect, a mixture comprising the microvesicles isolated from the biological sample and the control particles is created. Proteins from both the control particle and the microvesicles are extracted in a subsequent extraction step. Therefore, the recovery and/or quality of the control proteins from the control particles indicates the recovery and/or quality of proteins from the microvesicles, and therefore, high quality/quantity of the control proteins indicates high quality/quantity of the resulting protein preparation comprising the microvesicle proteins.

In some aspects, determining the amount of a control nucleic acid recovered comprises determining the expression level or copy number of the control nucleic acid after recovery. The expression level or the copy number of a control nucleic acid can be measured using any of a variety of art-recognized techniques, including, but not limited to, quantitative PCR and direct detection. In a non-limiting example, quantitative PCR analysis determines a Ct (cycle threshold) value for each reaction. In quantitative PCR, a positive reaction is detected by accumulation of a fluorescence signal. The Ct value is defined as the number of cycles required for the fluorescent signal to cross the threshold (i.e., exceeds background level). Ct levels are inversely proportional to the amount of target nucleic acid, or control nucleic acid, in the sample (i.e., the lower the Ct level, the greater the amount of control nucleic acid in the sample). Copy number of the control nucleic acid can be determined using methods known in the art, such as by generating and utilizing a calibration, or standard curve. In another non-limiting example, direct detection may be performed without an amplification step. Direct analysis may be performed with different methods including, but not limited to, the NanoString technology. NanoString technology enables identification and quantification of individual target molecules in a biological sample by attaching a color coded fluorescent reporter to each target molecule. These methods are described in Geiss et al. (see Geiss et al. *Nature Biotechnology,* 2008, 26(3): 317-325), which is incorporated herein by reference.

Copy number of a control nucleic acid can be determined using methods known in the art, such as by generating and utilizing a calibration, or standard curve. A standard curve can be generated using known concentrations and copy numbers of a standard nucleic acid in the subsequent quantification analysis (e.g., RT-PCR). The standard nucleic acid is similar or identical to the control nucleic acid of the control particle (e.g., has a similar or identical sequence). The standard target gene is quantified using the same methods to quantify the control target gene, as disclosed herein.

For example, a standard curve is generated using 10-fold dilutions of the standard nucleic acid. In some aspects, the standard curve is generated by using at least 2, 3, or 4 known concentrations/copy numbers of standard nucleic acids. The dilution samples of the standard nucleic acid is quantified by methods used herein, e.g., RT-PCR or quantitative PCR analysis. Preferably, the dilution series is analyzed on the same plate as the samples being analyzed for the quality of the microvesicle isolation and/or nucleic acid extraction methods. The calculated Ct or copy number from the quantitative PCR analysis of each dilution, with respect to the known concentration, is used to generate a standard curve. Extrapolation of the standard curve can be used to calculate the copy numbers of control particles after quantification of the control particles. By comparing the Ct values of the samples being analyzed for the quality of the isolation and/or extraction to the Ct values of the calibration curves, the exact copy number of the control particles recovered in the analyzed samples can be determined.

Copy numbers are calculated by fitting a curve of the following formula $$Ct = b + a * \log 10(Calibration\_Copies)$$

To the known calibration points on the dilution series on the plate to achieve the "calibration curve". Copy numbers for samples are then calculated by the formula $$Sample\_Copies = 10^{((Ct\_Sample-b)/a)}$$

This copy number calculation is done independently for each sample.

The calculated copy number or level of expression (i.e., Ct value) of the control nucleic acid is the amount or quantity of control particles recovered from the microvesicle isolation and/or nucleic acid extraction processes.

In some aspects, the quality of a microvesicle isolation and/or nucleic acid extraction is determined by comparing the expression level or calculated copy number of the recovered control particles (or control nucleic acids) to a pre-determined cutoff value. If the calculated amount of control particles is higher than the pre-determined cutoff value, then the quality of the micovesicle isolation and/or nucleic acid extraction is high. If the calculated amount of control particles is lower than the pre-determined cutoff value, then the quality of the microvesicle isolation and/or nucleic acid extraction is low. In another aspect, if the calculated amount of control particles is within 1%, 2%, 3%, 4%, 5%, 6%, 7%, 8%, 9%, 10%, 15%, 20%, 25%, 30%, 35%, 40%, 45% or 50% of the known quantity of the control particles first added to the biological sample prior to microvesicle isolation or nucleic acid extraction, then the quality of the isolation and/or extraction is high.

In some aspects, the predetermined cutoff threshold is a measured value from the quantification analysis, e.g., for quantitative PCR analysis, the pre-determined cutoff value is a Ct value. For example, the quality of the microvesicle isolation or nucleic acid extraction is high if the Ct value is below 25, below 26, below 27, below 28, below 29, or below 30. The quality of the microvesicle isolation or nucleic acid extraction is low if the Ct value is above 27, above 28, above 29, or 30.

In one aspect, the pre-determined range of values indicates that the biological sample has been successfully processed. In one aspect, the pre-determined range of values indicates that the microvesicle fraction has been successfully isolated. In one aspect, the pre-determined range of values indicates that the nucleic acids have been successfully processed. The pre-determined range of values is within 50%, 55%, 60%, 65%, 70%, 75%, 80%, 85%, 90%, or 95% of the number of control particles added to the sample prior to the microvesicle isolation or nucleic acid extraction steps. Preferably, the pre-determined range of values is greater than 80% of the number of control particles added to the sample. Preferably, the pre-determined range of values is greater than 85% of the number of control particles added to the sample. More preferably, the pre-determined range of values is greater than 90% of the number of control particles added to the sample. Most preferably, the pre-determined range of values is greater than 95% of the number of control particles added to the sample. In some aspects, the pre-determined range of values is indicated by the measured value from the quantification analysis, e.g., for quantitative PCR analysis, the pre-determined range of values is a Ct value, between 25-30, 20-30, 15-30, or 10-30.

In other aspects, the amount of control particles recovered (i.e., expression level or copy number of the control nucleic acid and/or control protein that is measured after recovery) is compared to a predetermined range of values. The pre-determined range of values is determined from a collection of reference samples (i.e., a patient cohort). The collection of reference samples have been processed using the microvesicle and nucleic acid extraction methods disclosed herein. A control particle is added to the sample prior to microvesicle isolation or prior to nucleic acid extraction. The mean of the levels of expression of the recovered or detected control nucleic acids (i.e., Ct values) and/or control protein from the collection of reference samples is calculated. The standard deviation from the mean of all the recovered or detected control nucleic acids and/or control proteins from the collection of reference samples is also calculated. The pre-determined range of values may be, for example, 1 standard deviation, 2 standard deviations, 3 standard deviations, 4 standard deviations, or 5 standard deviations from the mean expression level of the recovered control nucleic acids (i.e., Ct values) and/or control proteins from the collection of reference samples. Preferably, the pre-determined range of values is 3 standard deviations from the mean Ct value of the recovered control nucleic acids and/or control proteins from the reference samples. For example, if the Ct value of the recovered control nucleic acid and/or control proteins from a biological sample is within 3 standard deviations of the mean Ct value of the recovered control nucleic acids and/or control proteins of the collection of reference samples, then the extracted nucleic acids (or nucleic acid preparation) is of high quality and would be sufficient for further biomarker analysis. If the Ct value of the recovered control nucleic acids and/or control proteins from a biological sample is not within 3 standard deviations, or is outside 3 standard deviations, of the mean Ct value of the recovered control nucleic acids and/or control proteins of the collection of reference samples, then the extracted nucleic acids (or nucleic acid preparation) and/or extracted proteins are of low quality and would not be sufficient for further biomarker analysis. Low quality nucleic acid and/or protein preparations would not yield accurate or reliable results in biomarker analysis for diagnosis, prognosis, or therapy selection for a patient.

Samples in which no control nucleic acids are detected are deemed low quality and not suitable for further biomarker analysis.

Samples in which no control proteins are detected are deemed low quality and not suitable for further biomarker analysis.

The collection of reference samples may include healthy individuals that have not been diagnosed with a disease, for example, cancer. The collection of reference samples may include individuals that have been diagnosed with a disease, for example, cancer, or have a positive biopsy status. The cancer can be any kind of cancer or pre-cancerous condition. This includes, without limitation, epithelial cell cancers such as lung, ovarian, cervical, endometrial, breast, brain, colon and prostate cancers. Also included are gastrointestinal cancer, head and neck cancer, non-small cell lung cancer, cancer of the nervous system, retina cancer, skin cancer, liver cancer, pancreatic cancer, genital cancer and bladder cancer, melanoma, and leukemia.

The methods disclosed in the present disclosure can be used to determine whether the microvesicle preparations and/or nucleic acid preparations are of sufficient quality for further analysis of at least one disease-associated biomarker for diagnostic, prognostic, and therapeutic applications. For example, if the quality of the microvesicle isolation or nucleic acid extraction is determined to be high using the methods disclosed herein, then the extracted nucleic acids (or nucleic acid preparation) can be used for further analysis to aid in the diagnosis, prognosis or therapy selection for a disease or a medical condition. Conversely, if the quality of the microvesicle isolation or nucleic acid extraction is determined to be low using the methods disclosed herein, then the extracted nucleic acids should not be used for further analysis, as the low quality or efficiency from the isolation and/or extraction methods indicates that any further analysis may be inaccurate.

The present disclosure also provides methods for using multiple control particles for determining the quality or efficiency of multiple steps independently, such as microvesicle isolation and nucleic acid extraction, of the same sample. In this manner, for example, the quality of the microvesicle purification and the nucleic acid extraction can be evaluated in a single sample for a single analysis. For example, a known quantity of a first control particle comprising a first control nucleic acid and/or first control protein can be added prior to isolating a fraction comprising microvesicles from a biological sample and a known quantity of a second control particle comprising a second control nucleic acid and/or second control protein can be added prior to nucleic acid extraction. The amount of the first control nucleic acid and/or first control protein recovered and the amount of the second control nucleic acid and/or control protein recovered can be determined. The use of multiple, distinct control particles allows for the simultaneous analysis of the quality of microvesicle isolation and nucleic acid extraction for each sample.

Quantitative PCR can include, but is not limited to, reverse transcription quantitate PCR (RT-qPCR).

Microvesicle Isolation Methods

Several methods of isolating microvesicles from a biological sample have been described in the art. In some aspects, the biological sample is first processed to remove cells and other large contaminants. This first pre-processing step can be accomplished by using a 0.8 μm filter to separate cells and other cell debris from the microvesicles. Optionally, centrifugation (i.e., slow centrifugation) can be used to further separate contaminants from the microvesicles. Control particles are added to the pre-processed sample at a known quantity. Additional processing is performed to isolate a fraction containing microvesicles and control particles. Suitable additional processing steps include filtration concentrators and differential centrifugation. The fraction containing microvesicles and control particles is washed to remove additional contaminants at least once. The fraction may be washed once, twice, three times, four times, or five times using a physiological buffer, such as phosphate-buffered saline. RNase inhibitor was added to the fraction, preferably to the fraction located in the upper chamber of the filter concentrator. Lysis of the microvesicles and control particles can be optionally performed in the upper chamber of the filter concentrator.

The method of isolating microvesicles from a biological sample and extracting nucleic acids from the isolated microvesicles may be achieved by many methods. Some of these methods are described in publications WO 2009/100029, WO 2011/009104, WO2014/107571, WO2016/007755, WO2018/076018, and WO2017/197399, all of which are hereby incorporated in their entirety. In some aspects, the method comprises the following steps: removing cells from the bodily either by low speed centrifugation and/or filtration though a 0.8 μm filter; centrifuging the supernatant/filtrate at about 120,000 xg for about 0.5 hour at about 4° C.; treating the pellet with a pre-lysis solution, e.g., an RNase inhibitor and/or a pH buffered solution and/or a protease enzyme in sufficient quantities; and lysing the pellet for nucleic acid extraction. The lysis of microvesicles in the pellet and extraction of nucleic acids may be achieved with various methods known in the art (e.g., using commercially available kids (e.g., Qiagen) or phenol-chloroform extraction according to standard procedures and techniques known in the art). Control particles can be added, at least, prior to the microvesicle isolation step or prior to the RNA extraction step.

In some aspects, isolating microvesicles and/or control particles can comprise: contacting a biological sample with a capture surface under conditions sufficient to retain cell-free DNA, microvesicles and control particles on or in the capture surface, wherein the capture surface comprises one or more beads that are positively charged, one or more beads that are an anion exchanger functionalized with quaternary ammonium (R—CH$_2$—N$^+$(CH$_3$)$_3$), or one or more beads that are positively charged and functionalized with quaternary ammonium; contacting the capture surface with a lysis reagent while cell-free DNA, microvesicles and control particles are on or in the capture surface, thereby releasing the DNA and RNA from the sample and producing a homogenate; adding chloroform to the homogenate; and extracting the DNA, the RNA, or both the DNA and RNA from the homogenate.

In some aspects, isolating microvesicles and/or control particles can comprise: contacting a biological sample with a capture surface under conditions sufficient to retain cell-free DNA, microvesicles and control particles on or in the capture surface, wherein the capture surface comprises one or more beads that are positively charged, one or more beads that are an anion exchanger functionalized with quaternary ammonium (R—CH$_2$—N$^+$(CH$_3$)$_3$), or one or more beads that are positively charged and functionalized with quaternary ammonium; eluting the cell-free DNA, microvesicles and control particles from the capture surface; contacting the eluted cell-free DNA, microvesicles and control particles with a lysis reagent to release DNA and/or RNA from the microvesicles and control particles, thereby producing a homogenate; adding chloroform to the homogenate; and extracting the DNA, the RNA, or both the DNA and RNA from the homogenate.

In some aspects, isolating microvesicles and/or control particles can comprise: contacting a biological sample with a capture surface under conditions sufficient to retain cell-free DNA, microvesicles and control particles on or in the capture surface, wherein the capture surface comprises one or more membranes that are positively charged, one or more membranes that are an anion exchanger functionalized with quaternary ammonium (R—CH$_2$—N$^+$(CH$_3$)$_3$), or one or more membranes that are positively charged and functionalized with quaternary ammonium; contacting the capture surface with a lysis reagent while cell-free DNA, microvesicles and control particles are on or in the capture surface, thereby releasing the DNA and RNA from the sample and producing a homogenate; adding chloroform to the homogenate; and extracting the DNA, the RNA, or both the DNA and RNA from the homogenate.

In some aspects, isolating microvesicles and/or control particles can comprise: contacting a biological sample with a capture surface under conditions sufficient to retain cell-free DNA, microvesicles and control particles on or in the capture surface, wherein the capture surface comprises one or more membranes that are positively charged, one or more membranes that are an anion exchanger functionalized with quaternary ammonium (R—CH$_2$—N$^+$(CH$_3$)$_3$), or one or more membranes that are positively charged and functionalized with quaternary ammonium; eluting the cell-free DNA, microvesicles and control particles from the capture surface; contacting the eluted cell-free DNA, microvesicles and control particles with a lysis reagent to release DNA and/or RNA from the microvesicles and control particles, thereby producing a homogenate; adding chloroform to the homogenate; and extracting the DNA, the RNA, or both the DNA and RNA from the homogenate.

In some aspects, isolating microvesicles and/or control particles can comprise: contacting a biological sample with a capture surface under conditions sufficient to retain microvesicles and control particles on or in the capture surface, wherein the capture surface comprises one or more beads that are positively charged, one or more beads that are an anion exchanger functionalized with quaternary ammonium (R—CH$_2$—N$^+$(CH$_3$)$_3$), or one or more beads that are positively charged and functionalized with quaternary ammonium; contacting the capture surface with a lysis reagent while microvesicles and control particles are on or in the capture surface, thereby releasing the DNA and RNA from the sample and producing a homogenate; adding chloroform to the homogenate; and extracting the DNA, the RNA, or both the DNA and RNA from the homogenate.

In some aspects, isolating microvesicles and/or control particles can comprise: contacting a biological sample with a capture surface under conditions sufficient to retain microvesicles and control particles on or in the capture surface, wherein the capture surface comprises one or more beads that are positively charged, one or more beads that are an anion exchanger functionalized with quaternary ammonium (R—CH$_2$—N$^+$(CH$_3$)$_3$), or one or more beads that are positively charged and functionalized with quaternary ammonium; eluting the microvesicles and control particles from the capture surface; contacting the eluted microvesicles and control particles with a lysis reagent to release DNA and/or RNA from the microvesicles and control particles, thereby producing a homogenate; adding chloroform to the homogenate; and extracting the DNA, the RNA, or both the DNA and RNA from the homogenate.

In some aspects, isolating microvesicles and/or control particles can comprise: contacting a biological sample with a capture surface under conditions sufficient to retain microvesicles and control particles on or in the capture surface, wherein the capture surface comprises one or more membranes that are positively charged, one or more membranes that are an anion exchanger functionalized with quaternary ammonium (R—CH$_2$—N$^+$(CH$_3$)$_3$), or one or more membranes that are positively charged and functionalized with quaternary ammonium; contacting the capture surface with a lysis reagent while microvesicles and control particles are on or in the capture surface, thereby releasing the DNA and RNA from the sample and producing a homogenate; adding chloroform to the homogenate; and extracting the DNA, the RNA, or both the DNA and RNA from the homogenate.

In some aspects, isolating microvesicles and/or control particles can comprise: contacting a biological sample with a capture surface under conditions sufficient to retain microvesicles and control particles on or in the capture surface, wherein the capture surface comprises one or more membranes that are positively charged, one or more membranes that are an anion exchanger functionalized with quaternary ammonium (R—CH$_2$—N$^+$(CH$_3$)$_3$), or one or more membranes that are positively charged and functionalized with quaternary ammonium; eluting the microvesicles and control particles from the capture surface; contacting the eluted microvesicles and control particles with a lysis reagent to release DNA and/or RNA from the microvesicles and control particles, thereby producing a homogenate; adding chloroform to the homogenate; and extracting the DNA, the RNA, or both the DNA and RNA from the homogenate.

A lysis reagent can comprise a phenol-based lysis reagent. A lysis reagent can comprise a guanidine thiocyanate-based lysis reagent. In some aspects, a lysis reagent can be an elution buffer.

In some aspects, the conditions sufficient to retain cell-free DNA, microvesicles and/or control particles on a capture surface can comprise a chemical crowding agent to enhance binding of the cell-free DNA, microvesicles and/or control particles to the capture surface. In some aspects, the chemical crowding agent can be PEG.

In some aspects of the methods of the present disclosure, any step that releases or extracts nucleic acids (e.g. DNA and/or RNA) can further comprise releasing or extracting proteins. In some aspects of the methods of the present disclosure, any step that releases or extracts nucleic acids can alternatively comprise releasing or extracting proteins.

Additional methods of isolating microvesicles from a biological sample are known in the art. For example, a method of differential centrifugation is described by Raposo et al. (Raposo et al., 1996). Methods of anion exchange and/or gel permeation chromatography are described in U.S. Pat. Nos. 6,899,863 and 6,812,023. Methods of sucrose density gradients or organelle electrophoresis are described in U.S. Pat. No. 7,198,923. A method of magnetic activated cell sorting (MACS, Miltenyi) is described in (Taylor and Gercel-Taylor, 2008). A method of nanomembrane ultrafiltration concentrator is described in (Cheruvanky et al., 2007). Preferably, microvesicles can be identified and isolated from bodily fluid of a subject by a newly developed microchip technology that uses a unique microfluidic platform to efficiently and selectively separate tumor derived microvesicles. This technology, as described in a paper by Nagrath et al. (Nagrath et al., 2007), can be adapted to identify and separate microvesicles using similar principles of capture and separation as taught in the paper. Each of the foregoing references is incorporated by reference herein for its teaching of these methods.

The isolation methods of microvesicles having associated nucleic acids described herein also include: 1) Ultracentrifugation, often in combination with sucrose density gradients or sucrose cushions to float the relatively low-density microvesicles. Isolation of microvesicles by sequential differential centrifugations, combined with sucrose gradient ultracentrifugation, can provide high enrichment of microvesicles. 2) The use of volume-excluding polymer selected from the group consisting of polyethylene glycol, dextran, dextran sulfate, dextran acetate, polyvinyl alcohol, polyvinyl acetate, or polyvinyl sulfate; and wherein the molecular weight of the volume-excluding polymer is from 1000 to 35000 daltons performed in conjunction with the additive sodium chloride from 0-1M. 3) Size exclusion chromatography, for example, Sephadex™ G200 column matrix. 4) Selective immunoaffinity or charge-based capture using paramagnetic beads (including immuno-precipitation), for example, by using antibodies directed against the surface antigens including but not limited to EpCAM, CD326, KSA, TROP1. The selection antibodies can be conjugated to paramagnetic microbeads. 5) Direct precipitation with chaotropic agents such as guanidinium thiocyanate.

Isolation of microvesicles can be achieved via a membrane as the capture surface, although it should be understood that the format of the capturing surface, e.g., beads or a filter (also referred to herein as a membrane), does not affect the ability of the methods provided herein to efficiently capture microvesicles from a biological sample.

In aspects where the capture surface is a membrane, the device for isolating the extracellular vesicle fraction from a biological sample contains at least one membrane. In some aspects, the device comprises one, two, three, four, five or six membranes. In some aspects, the device comprises three membranes. In aspects where the device comprises more than one membrane, the membranes are all directly adjacent to one another at one end of the column. In aspects where the device comprises more than one membrane, the membranes are all identical to each other, i.e., are of the same charge and/or have the same functional group.

It should be noted that capture by filtering through a pore size smaller than the microvesicles is not the primary mechanism of capture by the methods provided herein. However, filter pore size is nevertheless very important, e.g. because mRNA gets stuck on a 20 nm filter and cannot be recovered, whereas microRNAs can easily be eluted off, and e.g. because the filter pore size is an important parameter in available surface capture area.

The methods provided herein use samples isolated by any of a variety of capture surfaces. In some aspects, the capture surface is a membrane, also referred to herein as a filter or a membrane filter. In some aspects, the capture surface is a commercially available membrane. In some aspects, the capture surface is a charged commercially available membrane. In some aspects, the capture surface is neutral. In some aspects, the capture surface is selected from Mustang® Ion Exchange Membrane from PALL Corporation; Vivapure® Q membrane from Sartorius AG; Sartobind Q, or Vivapure® Q Maxi H; Sartobind® D from Sartorius AG, Sartobind (S) from Sartorius AG, Sartobind® Q from Sartorius AG, Sartobind® IDA from Sartorius AG, Sartobind® Aldehyde from Sartorius AG, Whatman® DE81 from Sigma, Fast Trap Virus Purification column from EMD Millipore; Thermo Scientific* Pierce Strong Cation and Anion Exchange Spin Columns.

In aspects where the capture surface is charged, the capture surface can be a charged filter selected from the group consisting of 0.65 µm positively charged Q PES vacuum filtration (Millipore), 3-5 µm positively charged Q RC spin column filtration (Sartorius), 0.8 µm positively charged Q PES homemade spin column filtration (Pall), 0.8 µm positively charged Q PES syringe filtration (Pall), 0.8 µm negatively charged S PES homemade spin column filtration (Pall), 0.8 µm negatively charged S PES syringe filtration (Pall), and 50 nm negatively charged nylon syringe filtration (Sterlitech). In some aspects, the charged filter is not housed in a syringe filtration apparatus, as nucleic acid can be harder to get out of the filter in these aspects. In some aspects, the charged filter is housed at one end of a column.

In aspects where the capture surface is a membrane, the membrane can be made from a variety of suitable materials. In some aspects, the membrane is polyethersulfone (PES) (e.g., from Millipore or PALL Corp.). In some aspects, the membrane is regenerated cellulose (RC) (e.g., from Sartorius or Pierce).

In some aspects, the capture surface is a positively charged membrane. In some aspects, the capture surface is a Q membrane, which is a positively charged membrane and is an anion exchanger with quaternary amines. For example, the Q membrane is functionalized with quaternary ammonium, $R-CH_2-N^+(CH_3)_3$. In some aspects, the capture surface is a negatively charged membrane. In some aspects, the capture surface is an S membrane, which is a negatively charged membrane and is a cation exchanger with sulfonic acid groups. For example, the S membrane is functionalized with sulfonic acid, $R-CH_2-SO_3^-$. In some aspects, the capture surface is a D membrane, which is a weak basic anion exchanger with diethylamine groups, $R-CH_2-NH^+(C_2H_5)_2$. In some aspects, the capture surface is a metal chelate membrane. For example, the membrane is an IDA membrane, functionalized with minodiacetic acid $-N(CH_2COOH^-)_2$. In some aspects, the capture surface is a microporous membrane, functionalized with aldehyde groups, $-CHO$. In other aspects, the membrane is a weak basic anion exchanger, with diethylaminoethyl (DEAE) cellulose. Not all charged membranes are suitable for use in the methods provided herein, e.g., RNA isolated using Sartorius Vivapure S membrane spin column showed RT-qPCR inhibition and, thus, unsuitable for PCR related downstream assay.

In aspects where the capture surface is charged, microvesicles can be isolated with a positively charged filter.

In aspects where the capture surface is charged, the pH during extracellular vesicle capture is a pH<7. In some aspects, the pH is greater than 4 and less than or equal to 8.

In aspects where the capture surface is a positively charged Q filter, the buffer system includes a wash buffer comprising 250 mM Bis Tris Propane, pH 6.5-7.0. In aspects where the capture surface is a positively charged Q filter, the lysis buffer is a GTC-based reagent. In aspects where the capture surface is a positively charged Q filter, the lysis buffer is present at one volume. In aspects where the capture surface is a positively charged Q filter, the lysis buffer is present at more than one volume.

Depending on the membrane material, the pore sizes of the membrane range from 3 μm to 20 nm. For example, in aspects where the capture surface is a commercially available PES membrane, the membrane has a pore size of 20 nm (Exomir), 0.65 μm (Millipore) or 0.8 μm (Pall). In aspects where the capture surface is a commercially available RC membrane, the membrane has a pore size in the range of 3-5 μm (Sartorius, Pierce).

The surface charge of the capture surface can be positive, negative or neutral. In some aspects, the capture surface is a positively charged bead or beads.

In some aspects, the sample is not pre-processed prior to isolation of microvesicles and extraction of nucleic acids, e.g., DNA and/or DNA and RNA, from the biological sample.

In some aspects, the sample is subjected to a pre-processing step prior to isolation, purification or enrichment of the microvesicles is performed to remove large unwanted particles, cells and/or cell debris and other contaminants present in the biological sample. The pre-processing steps may be achieved through one or more centrifugation steps (e.g., differential centrifugation) or one or more filtration steps (e.g., ultrafiltration), or a combination thereof.

Where more than one centrifugation pre-processing steps are performed, the biological sample may be centrifuged first at the lower speed and then at the higher speed. If desired, further suitable centrifugation pre-processing steps may be carried out. Alternatively, or in addition to the one or more centrifugation pre-processing steps, the biological sample may be filtered. For example, a biological sample may be first centrifuged at 20,000 g for 1 hour to remove large unwanted particles; the sample can then be filtered, for example, through a 0.8 μm filter.

In some aspects, the sample is pre-filtered to exclude particles larger than 0.8 μm. In some aspects, the sample includes an additive such as EDTA, sodium citrate, and/or citrate-phosphate-dextrose. In some aspects, the sample does not contain heparin, as heparin can negatively impact RT-qPCR and other nucleic acid analysis. In some aspects, the sample is mixed with a buffer prior to purification and/or nucleic acid isolation and/or extraction. In some aspects, the buffer is a binding buffer.

In some aspects, one or more centrifugation steps are performed before or after contacting the biological sample with the capture surface to separate microvesicles and concentrate the microvesicles isolated from the biological fraction. To remove large unwanted particles, cells, and/or cell debris, the samples may be centrifuged at a low speed of about 100-500 g, for example, in some aspects, about 250-300 g. Alternatively or in addition, the samples may be centrifuged at a higher speed. Suitable centrifugation speeds are up to about 200,000 g; for example, from about 2,000 g to less than about 200,000 g. Speeds of above about 15,000 g and less than about 200,000 g or above about 15,000 g and less than about 100,000 g or above about 15,000 g and less than about 50,000 g are used in some aspects. Speeds of from about 18,000 g to about 40,000 g or about 30,000 g; and from about 18,000 g to about 25,000 g are more preferred. In some aspects, a centrifugation speed of about 20,000 g. Generally, suitable times for centrifugation are from about 5 minutes to about 2 hours, for example, from about 10 minutes to about 1.5 hours, or from about 15 minutes to about 1 hour. A time of about 0.5 hours may be used. It is sometimes useful, in some aspects, to subject the biological sample to centrifugation at about 20,000 g for about 0.5 hours. However, the above speeds and times can suitably be used in any combination (e.g., from about 18,000 g to about 25,000 g, or from about 30,000 g to about 40,000 g for about 10 minutes to about 1.5 hours, or for about 15 minutes to about 1 hour, or for about 0.5 hours, and so on). The centrifugation step or steps may be carried out at below-ambient temperatures, for example at about 0-10° C., for example, about 1-5° C., e.g., about 3° C. or about 4° C.

In some aspects, one or more filtration steps are performed before or after contacting the biological sample with the capture surface. A filter having a size in the range about 0.1 to about 1.0 μm may be employed, for example, about 0.8 μm or 0.22 μm. The filtration may also be performed with successive filtrations using filters with decreasing porosity.

In some aspects, one or more concentration steps are performed, in order to reduce the volumes of sample to be treated during the chromatography stages, before or after contacting the biological sample with the capture surface. Concentration may be through centrifugation of the sample at high speeds, e.g. between 10,000 and 100,000 g, to cause the sedimentation of the microvesicles. This may consist of a series of differential centrifugations. The microvesicles in the pellet obtained may be reconstituted with a smaller volume and in a suitable buffer for the subsequent steps of the process. The concentration step may also be performed by ultrafiltration. In fact, this ultrafiltration both concentrates the biological sample and performs an additional purification of the extracellular vesicle fraction. In some aspects, the filtration is an ultrafiltration, for example, a tangential ultrafiltration. Tangential ultrafiltration consists of concentrating and fractionating a solution between two compartments (filtrate and retentate), separated by membranes of determined cut-off thresholds. The separation is carried out by applying a flow in the retentate compartment and a transmembrane pressure between this compartment and the filtrate compartment. Different systems may be used to perform the ultrafiltration, such as spiral membranes (Millipore, Amicon), flat membranes or hollow fibers (Amicon, Millipore, Sartorius, Pall, GF, Sepracor). Within the scope of the disclosure, the use of membranes with a cut-off threshold below 1000 kDa, for example, in some aspects, between 100 kDa and 1000 kDa, or for example, in some aspects, between 100 kDa and 600 kDa, is advantageous.

In some aspects, one or more size-exclusion chromatography step or gel permeation chromatography steps are performed before or after contacting the biological sample with the capture surface. To perform the gel permeation chromatography step, a support selected from silica, acrylamide, agarose, dextran, ethylene glycol-methacrylate co-polymer or mixtures thereof, e.g., agarose-dextran mixtures, are used in some aspects. For example, such supports include, but are not limited to: SUPERDEX® 200HR (Pharmacia), TSK G6000 (TosoHaas) or SEPHACRYL® S (Pharmacia).

In some aspects, one or more affinity chromatography steps are performed before or after contacting the biological sample with the capture surface. Some microvesicles can also be characterized by certain surface molecules. Because microvesicles form from budding of the cell plasma membrane, these microvesicles often share many of the same surface molecules found on the cells they originated from. As used herein, "surface molecules" refers collectively to antigens, proteins, lipids, carbohydrates, and markers found on the surface or in or on the membrane of the microvesicle. These surface molecules can include, for example, receptors, tumor-associated antigens, membrane protein modifications (e.g., glycosylated structures). For example, microvesicles that bud from tumor cells often display tumor-associated antigens on their cell surface. As such, affinity chromatography or affinity exclusion chromatography can also be utilized in combination with the methods provided herein to isolate, identify, and or enrich for specific populations of microvesicles from a specific donor cell type (Al-Nedawi et al., 2008; Taylor and Gercel-Taylor, 2008). For example, tumor (malignant or non-malignant) microvesicles carry tumor-associated surface antigens and may be detected, isolated and/or enriched via these specific tumor-associated surface antigens. In one example, the surface antigen is epithelial cell adhesion molecule (EpCAM), which is specific to microvesicles from carcinomas of lung, colorectal, breast, prostate, head and neck, and hepatic origin, but not of hematological cell origin (Balzar et al., 1999; Went et al., 2004). Additionally, tumor-specific microvesicles can also be characterized by the lack of certain surface markers, such as CD80 and CD86. In these cases, microvesicles with these markers may be excluded for further analysis of tumor specific markers, e.g., by affinity exclusion chromatography. Affinity chromatography can be accomplished, for example, by using different supports, resins, beads, antibodies, aptamers, aptamer analogs, molecularly imprinted polymers, or other molecules known in the art that specifically target desired surface molecules on microvesicles.

In some aspects, the microvesicles isolated from a bodily fluid are enriched for those originating from a specific cell type, for example, lung, pancreas, stomach, intestine, bladder, kidney, ovary, testis, skin, colorectal, breast, prostate, brain, esophagus, liver, placenta, fetus cells. Because the microvesicles often carry surface molecules such as antigens from their donor cells, surface molecules may be used to identify, isolate and/or enrich for microvesicles from a specific donor cell type (Al-Nedawi et al., 2008; Taylor and Gercel-Taylor, 2008). In this way, microvesicles originating from distinct cell populations can be analyzed for their RNA content. For example, tumor (malignant and nonmalignant) microvesicles carry tumor-associated surface antigens and may be detected, isolated and/or enriched via these specific tumor-associated surface antigens. In one example, the surface antigen is epithelial-cell-adhesion-molecule (EpCAM), which is specific to microvesicles from carcinomas of lung, colorectal, breast, prostate, head and neck, and hepatic origin, but not of hematological cell origin (Balzar et al., 1999; Went et al., 2004). In another example, the surface antigen is CD24, which is a glycoprotein specific to urine microvesicles (Keller et al., 2007). In yet another example, the surface antigen is selected from a group of molecules CD70, carcinoembryonic antigen (CEA), EGFR, EGFRvIII and other variants, Fas ligand, TRAIL, tranferrin receptor, p38.5, p97 and HSP72. Additionally, tumor specific microvesicles may be characterized by the lack of surface markers, such as CD80 and CD86.

The isolation of microvesicles from specific cell types can be accomplished, for example, by using antibodies, aptamers, aptamer analogs or molecularly imprinted polymers specific for a desired surface antigen. In some aspects, the surface antigen is specific for a cancer type. In some aspects, the surface antigen is specific for a cell type which is not necessarily cancerous. One example of a method of microvesicle separation based on cell surface antigen is provided in U.S. Pat. No. 7,198,923. As described in, e.g., U.S. Pat. Nos. 5,840,867 and 5,582,981, WO2003/050290 and a publication by Johnson et al. (Johnson et al., 2008), aptamers and their analogs specifically bind surface molecules and can be used as a separation tool for retrieving cell type-specific microvesicles. Molecularly imprinted polymers also specifically recognize surface molecules as described in, e.g., U.S. Pat. Nos. 6,525,154, 7,332,553 and 7,384,589 and a publication by Bossi et al. (Bossi et al., 2007) and are a tool for retrieving and isolating cell type-specific microvesicles. Each of the foregoing reference is incorporated herein for its teaching of these methods.

Nucleic Acid Extraction Methods

In some aspects, it may be beneficial or otherwise desirable to amplify the nucleic acid of the microvesicle prior to analyzing it. Methods of nucleic acid amplification are commonly used and generally known in the art, many examples of which are described herein. If desired, the amplification can be performed such that it is quantitative. Quantitative amplification will allow quantitative determination of relative amounts of the various nucleic acids, to generate a genetic or expression profile.

In some aspects, the nucleic acid extracted from the microvesicles is DNA. In some aspects, the nucleic acid extracted from the microvesicles is RNA. RNA may include messenger RNAs, transfer RNAs, ribosomal RNAs, small RNAs (non-protein-coding RNAs, non-messenger RNAs), microRNAs, piRNAs, exRNAs, snRNAs and snoRNAs.

In some aspects, the RNA is preferably reverse-transcribed into complementary DNA (cDNA) before further amplification. RNAs are then preferably reverse-transcribed into complementary DNAs before further amplification. Such reverse transcription may be performed alone or in combination with an amplification step. One example of a method combining reverse transcription and amplification steps is reverse transcription polymerase chain reaction (RT-PCR), which may be further modified to be quantitative, e.g., quantitative RT-PCR as described in U.S. Pat. No. 5,639,606, which is incorporated herein by reference for this teaching. The extracted nucleic acids or complementary DNA can be analyzed for diagnostic purposes by nucleic acid amplification.

Nucleic acid amplification methods include, without limitation, polymerase chain reaction (PCR) (U.S. Pat. No. 5,219,727) and its variants such as in situ polymerase chain reaction (U.S. Pat. No. 5,538,871), quantitative polymerase chain reaction (U.S. Pat. No. 5,219,727), nested polymerase chain reaction (U.S. Pat. No. 5,556,773), self-sustained sequence replication and its variants (Guatelli et al., 1990), transcriptional amplification system and its variants (Kwoh et al., 1989), Qb Replicase and its variants (Miele et al., 1983), cold-PCR (Li et al., 2008), BEAMing (Li et al., 2006) or any other nucleic acid amplification methods, followed by the detection of the amplified molecules using techniques well known to those of skill in the art. Especially useful are those detection schemes designed for the detection of nucleic acid molecules if such molecules are present in very low numbers. The foregoing references are incorporated herein for their teachings of these methods. In some aspects, the step of nucleic acid amplification is not performed. Instead, the extract nucleic acids are analyzed directly (e.g., through next-generation sequencing).

The analysis of nucleic acids present in the isolated particles is quantitative and/or qualitative. For quantitative analysis, the amounts or expression levels, either relative or absolute, of specific nucleic acids of interest within the isolated particles are measured with methods known in the art. For qualitative analysis, the species of specific nucleic acids of interest within the isolated particles, whether wild type or variants, are identified with methods known in the art.

Following the isolation of microvesicles from a biological sample, nucleic acid may be extracted from the isolated or enriched microvesicle fraction. To achieve this, the microvesicles may first be lysed. The lysis of microvesicles and extraction of nucleic acids may be achieved with various methods known in the art, including those described in PCT Publication Nos. WO 2016/007755 and WO 2014/107571, the contents of each of which are hereby incorporated by reference in their entirety. Nucleic acid extraction may be achieved using protein precipitation according to standard procedures and techniques known in the art. Such methods may also utilize a nucleic acid-binding column to capture the nucleic acids contained within the microvesicles. Once bound, the nucleic acids can then be eluted using a buffer or solution suitable to disrupt the interaction between the nucleic acids and the binding column, thereby eluting the nucleic acids.

Exosomal derived nucleic acids can include RNA or DNA, either individually or as a mixture of RNA and DNA. Exosomal derived nucleic acids can include material either contained within or bound to the outer surface of microvesicles. The DNA component can be exosomal or other cell-free sources (cfDNA).

Where an microvesicle fraction is utilized, isolation and extraction of nucleic acids, e.g., DNA and/or DNA and nucleic acids including at least RNA from a sample using the following general procedure. First, the nucleic acids in the sample, e.g., the DNA and/or the DNA and the extracellular vesicle fraction, are bound to a capture surface such as a membrane filter, and the capture surface is washed. Then, an elution reagent is used to perform on-membrane lysis and release of the nucleic acids, e.g., DNA and/or DNA and RNA, thereby forming an eluate. The eluate is then contacted with a protein precipitation buffer that includes a transition metal and a buffering agent. The cfDNA and/or DNA and nucleic acids include at least the RNA from the microvesicles is then isolated from the protein-precipitated eluate using any of a variety of art-recognized techniques, such as, for example, binding to a silica column followed by washing and elution.

The elution buffer may comprise a denaturing agent, a detergent, a buffer substance, and/or combinations thereof to maintain a defined solution pH. The elution buffer may include a strong denaturing agent, or even a strong denaturing agent and a reduction agent.

Diagnostic Methods

The present disclosure also includes methods for microvesicle nucleic acid analysis with the presence of control particles for (i) aiding in the diagnosis of a subject, (ii) monitoring the progress or reoccurrence of a disease or other medical condition in a subject, or (iii) aiding in the evaluation of treatment efficacy for a subject undergoing or contemplating treatment for a disease or other medical condition; wherein the presence or absence of one or more biomarkers in the nucleic acid extraction obtained from the method is determined, and the one or more biomarkers are associated with the diagnosis, progress or reoccurrence, or treatment efficacy, respectively, of a disease or other medical condition.

The one or more biomarkers can be one or a collection of genetic aberrations, which is used herein to refer to the nucleic acid amounts as well as nucleic acid variants within the nucleic acid-containing particles. Specifically, genetic aberrations include, without limitation, over-expression of a gene (e.g., an oncogene) or a panel of genes, under-expression of a gene (e.g., a tumor suppressor gene such as p53 or RB) or a panel of genes, alternative production of splice variants of a gene or a panel of genes, gene copy number variants (CNV) (e.g., DNA double minutes) (Hahn, 1993), nucleic acid modifications (e.g., methylation, acetylation and phosphorylations), single nucleotide polymorphisms (SNPs), chromosomal rearrangements (e.g., inversions, deletions and duplications), and mutations (insertions, deletions, duplications, missense, nonsense, synonymous or any other nucleotide changes) of a gene or a panel of genes, which mutations, in many cases, ultimately affect the activity and function of the gene products, lead to alternative transcriptional splice variants and/or changes of gene expression level, or combinations of any of the foregoing.

The determination of such genetic aberrations can be performed by a variety of techniques known to the skilled practitioner. For example, expression levels of nucleic acids, alternative splicing variants, chromosome rearrangement and gene copy numbers can be determined by microarray analysis (see, e.g., U.S. Pat. Nos. 6,913,879, 7,364,848, 7,378,245, 6,893,837 and 6,004,755) and quantitative PCR. Particularly, copy number changes may be detected with the Illumina Infinium II whole genome genotyping assay or Agilent Human Genome CGH Microarray (Steemers et al., 2006). Nucleic acid modifications can be assayed by methods described in, e.g., U.S. Pat. No. 7,186,512 and patent publication WO2003/023065. Particularly, methylation profiles may be determined by Illumina DNA Methylation OMA003 Cancer Panel. SNPs and mutations can be detected by hybridization with allele-specific probes, enzymatic mutation detection, chemical cleavage of mismatched heteroduplex (Cotton et al., 1988), ribonuclease cleavage of mismatched bases (Myers et al., 1985), mass spectrometry (U.S. Pat. Nos. 6,994,960, 7,074,563, and 7,198,893), nucleic acid sequencing, single strand conformation polymorphism (SSCP) (Orita et al., 1989), denaturing gradient gel electrophoresis (DGGE)(Fischer and Lerman, 1979a; Fischer and Lerman, 1979b), temperature gradient gel electrophoresis (TGGE) (Fischer and Lerman, 1979a; Fischer and Lerman, 1979b), restriction fragment length polymorphisms (RFLP) (Kan and Dozy, 1978a; Kan and Dozy, 1978b), oligonucleotide ligation assay (OLA), allele-specific PCR (ASPCR) (U.S. Pat. No. 5,639,611), ligation chain reaction (LCR) and its variants (Abravaya et al., 1995; Landegren et al., 1988; Nakazawa et al., 1994), flow-cytometric heteroduplex analysis (WO/2006/113590) and combinations/modifications thereof. Notably, gene expression levels may be determined by the serial analysis of gene expression (SAGE) technique (Velculescu et al., 1995). In general, the methods for analyzing genetic aberrations are reported in numerous publications, not limited to those cited herein, and are available to skilled practitioners. The appropriate method of analysis will depend upon the specific goals of the analysis, the condition/history of the patient, and the specific cancer(s), diseases or other medical conditions to be detected, monitored or treated. The forgoing references are incorporated herein for their teaching of these methods.

Many biomarkers may be associated with the presence or absence of a disease or other medical condition in a subject. Therefore, detection of the presence or absence of such biomarkers in a nucleic acid extraction from isolated particles, according to the methods disclosed herein, may aid diagnosis of the disease or other medical condition in the subject. For example, as described in WO 2009/100029, detection of the presence or absence of the EGFRvIII mutation in nucleic acids extracted from microvesicles isolated from a patient serum sample may aid in the diagnosis and/or monitoring of glioblastoma in the patient. This is so because the expression of the EGFRvIII mutation is specific to some tumors and defines a clinically distinct subtype of glioma (Pelloski et al., 2007). For another example, as described in WO 2009/100029, detection of the presence or absence of the TMPRSS2-ERG fusion gene and/or PCA-3 in nucleic acids extracted from microvesicles isolated from a patient urine sample may aid in the diagnosis of prostate cancer in the patient. For another example, detection of presence or absence of the combination of ERG and AMACR in a bodily fluid may aid in the diagnosis of cancer in a patient.

Further, many biomarkers may help disease or medical status monitoring in a subject. Therefore, the detection of the presence or absence of such biomarkers in a nucleic acid extraction from isolated particles, according to the methods disclosed herein, may aid in monitoring the progress or reoccurrence of a disease or other medical condition in a subject. For example, as described in WO 2009/100029, the determination of matrix metalloproteinase (MMP) levels in nucleic acids extracted from microvesicles isolated from an organ transplantation patient may help to monitor the post-transplantation condition, as a significant increase in the expression level of MMP-2 after kidney transplantation may indicate the onset and/or deterioration of post-transplantation complications. Similarly, a significantly elevated level of MMP-9 after lung transplantation, suggests the onset and/or deterioration of bronchiolitis obliterans syndrome.

Many biomarkers have also been found to influence the effectiveness of treatment in a patient. Therefore, the detection of the presence or absence of such biomarkers in a nucleic acid extraction from isolated particles, according to the methods disclosed herein, may aid in evaluating the efficacy of a given treatment in a given patient. For example, as disclosed in Table 1 in the publication by Furnari et. al. (Furnari et al., 2007), biomarkers, e.g., mutations in a variety of genes, affect the effectiveness of specific medicines used in chemotherapy for treating brain tumors. The identification of these biomarkers in nucleic acids extracted from isolated particles from a biological sample from a patient may guide the selection of treatment for the patient.

In some aspects, the disease or other medical condition is a neoplastic disease or condition (e.g., cancer or cell proliferative disorder), a metabolic disease or condition (e.g., diabetes, inflammation, perinatal conditions or a disease or condition associated with iron metabolism), a neurological disease or condition, an immune disorder or condition, a post transplantation condition, a fetal condition, or a pathogenic infection or disease or condition associated with an infection.

Kits

The present disclosure provides kits for isolating microvesicles and microvesicle-derived nucleic acids from a biological sample and distinguishing the quality of a microvesicle isolation or nucleic acid extraction for the subsequent analysis or detection of at least one biomarker associated with a disease or medical condition.

In some aspects, a kit of the present disclosure comprises a known quantity of a control particles comprising at least one control nucleic acid. In some aspects, a kit of the present disclosure comprises a known quantity of a control particles comprising at least one control protein. In some aspects, a kit of the present disclosure comprises a known quantity of a control particles comprising at least one control nucleic acid and at least one control protein.

A kit of the present disclosure can comprise control nucleic acid-specific primers.

A kit of the present disclosure can comprise control nucleic acid-specific probes, A kit of the present disclosure can comprise a set of known concentration dilutions of the control nucleic acid for generating a standard curve.

A kit of the present disclosure can comprise instructions for using a control particle in the isolation of a microvesicle fraction from a biological sample and extraction of nucleic acids from the microvesicle fraction.

Optionally, a kit of the present disclosure may also include a lysis buffer, a filtration concentrator, a DNase or RNase inhibitor, to increase the quality or purity of nucleic acid extraction.

Definitions

As used herein, the term "biological sample" refers to a sample that contains biological materials such as a DNA, a RNA and/or a protein. In some aspects, the biological sample may suitably comprise a bodily fluid from a subject. The bodily fluids can be fluids isolated from anywhere in the body of the subject, preferably a peripheral location, including but not limited to, for example, blood, plasma, serum, urine, sputum, spinal fluid, cerebrospinal fluid, pleural fluid, nipple aspirates, lymph fluid, fluid of the respiratory, intestinal, and genitourinary tracts, tear fluid, saliva, breast milk, fluid from the lymphatic system, semen, cerebrospinal fluid, intra-organ system fluid, ascitic fluid, tumor cyst fluid, amniotic fluid and combinations thereof. In some aspects, the preferred body fluid for use as the biological sample is urine. In other aspects, the preferred body fluid is serum. In still other aspects, the preferred body fluid is cerebrospinal fluid.

Suitably a biological sample volume of about 0.1 ml to about 30 ml fluid may be used. The volume of fluid may depend on a few factors, e.g., the type of fluid used. For example, the volume of serum samples may be about 0.1 ml to about 2 ml, preferably about 1ml. The volume of urine samples may be about 10 ml to about 30 ml, preferably about 20 ml.

The term "subject" is intended to include all animals shown to or expected to have nucleic acid-containing particles. In some aspects, the subject is a mammal, a human or nonhuman primate, a dog, a cat, a horse, a cow, other farm animals, or a rodent (e.g. mice, rats, guinea pig. etc.). A human subject may be a normal human being without observable abnormalities, e.g., a disease. A human subject may be a human being with observable abnormalities, e.g., a disease. The observable abnormalities may be observed by the human being himself, or by a medical professional. The term "subject", "patient", and "individual" are used interchangeably herein.

Example #1—MHV Particles can be Isolated with High Efficiency from Biological Samples The following is an example that demonstrates that MHV particles can be co-isolated with microvesicles from biological samples with greater efficiency than protein-based particles such as Q-beta bacteriophage particles.

The experimental setup is shown in FIG. 2. Briefly, four different experimental conditions were tested. In the first experimental condition, referred to as the Urine condition in FIG. 2, 10 μl of a solution comprising MHV particles and 10 μl of a solution comprising Q-beta bacteriophage particles were added to 20 ml urine samples. The urinary microvesicles, MHV particles and Q-beta bacteriophage particles were then isolated by contacting the sample with a positively charged, bead-based capture surface functionalized with quaternary ammonium, as described above. Nucleic acid was extracted from the microvesicles, MHV particles and Q-beta bacteriophage particles by contacting the capture surface with a lysis and elution buffer (LEB). The eluate was then analyzed using quantitative reverse transcription PCR (RT-qPCR) to determine the CT value for the Q-beta bacteriophage RNA, the MHV RNA, an mRNA that is present in the urinary microvesicles and a reverse transcription control RNA.

In the second experimental condition, referred to as the LEB with Urine Background (LEB w/ urine bkgrd.) condition in FIG. 2, microvesicles were first isolated from 20 ml urine samples by contacting the sample with a positively charged, bead-based capture surface functionalized with quaternary ammonium, as described above. The isolated microvesicles were then contacted with a mixture comprising lysis and elution buffer, as well as 10 μl of a solution comprising MHV particles and 10 μl of a solution comprising Q-beta bacteriophage particles. The eluate was then analyzed using RT-qPCR to determine the CT value for the Q-beta bacteriophage RNA, the MHV RNA, an mRNA that is present in the urinary microvesicles and a reverse transcription control RNA.

In the third experimental condition, referred to as the LEB condition in FIG. 2, a lysis and elution buffer was mixed with 10 μl of a solution comprising MHV particles and 10 μl of a solution comprising Q-beta bacteriophage particles. The eluate was then analyzed using RT-qPCR to determine the CT value for the Q-beta bacteriophage RNA, the MHV RNA, an mRNA that is present in urinary microvesicles and a reverse transcription control RNA.

In the fourth experimental condition, referred to as the RT condition in FIG. 2, 10 μl of a solution comprising MHV particles and 10 μl of a solution comprising Q-beta bacteriophage particles were denatured at 95° C. for 5 minutes. The denatured particles were then analyzed using RT-qPCR to determine the CT value for the Q-beta bacteriophage RNA, the MHV RNA, an mRNA that is present in urinary microvesicles and a reverse transcription control RNA.

The results of the RT-qPCR analysis in the above experiments are shown in FIG. 3. The results in FIG. 3 demonstrate that although both MHV particles and Q-beta bacteriophage particles can be isolated from urine samples, MHV particles were isolated with a greater efficiency, as evidenced by lower CT values for MHV1 RNA in the Urine condition. Thus, these results indicate that MHV can be used as a control particle for microvesicle and microvesicular nucleic acid isolation procedures, and that MHV demonstrates superior properties as compared to Q-beta bacteriophage.

Example #2—MHV can be Isolated from Biological Samples

The following is an example that demonstrates that MHV can be co-isolated with microvesicles from biological samples.

The experimental setup is shown in FIG. 4. Briefly, three different experimental conditions were tested. In the first experimental condition, referred to as the Urine condition in FIG. 4, 10 μl of a solution comprising MHV particles was added to a 20 ml urine sample. The urinary microvesicles and the MHV particles were then isolated using a positively charged, spin-filter based capture surface functionalized with quaternary ammonium, as described above. Nucleic acid was then extracted from the microvesicles and MHV particles by contacting the capture surface with QIAzol reagent. The eluate was then analyzed using RT-qPCR to determine the CT value for the MHV RNA and an mRNA that is present in the urinary microvesicles.

In the second experimental condition, referred to as the QIAzol with urine background (QIAzol w/ urine bkgrd.) condition in FIG. 4, microvesicles were first isolated from a 20 ml urine sample using a positively charged, spin-filter based capture surface functionalized with quaternary ammonium, as described above. The isolated microvesicles were then contacted with a QIAzol reagent to lyse the isolated microvesicles. 10 μl of a solution comprising MHV particles was then added to the lysis reaction. The eluate was then analyzed using RT-qPCR to determine the CT value for the MHV RNA and an mRNA that is present in the urinary microvesicles.

In the third experimental condition, referred to as the QIAzol condition in FIG. 4, 10 μl of a solution comprising MHV particles was contacted with QIAzol reagent. The mixture was then analyzed using RT-qPCR to determine the CT value for the MHV RNA, an mRNA that is present in the urinary microvesicles.

The results of the RT-qPCR analysis in the above experiments are shown in FIG. 5. The results in FIG. 5 show that the MHV particles were efficiently isolated and the MHV RNA measured whether the MHV particles were introduced prior to microvesicle isolation (Urine condition) or after microvesicle isolation (QIAzol w/ urine bkgrd. condition). Thus, these results indicate that MHV can be used as a control particle for microvesicle and microvesicular nucleic acid isolation procedures.

Example #3—MHV can be Isolated with High Efficiency from Biological Samples

The following is an example that demonstrates that MHV can be co-isolated with microvesicles from biological samples with greater efficiency than protein-based particles such as Q-beta bacteriophage particles.

The experimental setup is shown in FIG. 6. Briefly, three different experimental conditions were tested. In the first experimental condition, referred to as the Plasma condition in FIG. 6, 10 μl of a solution comprising MHV particles and 10 μl of a solution comprising Q-beta bacteriophage particles were added to 2 ml plasma samples. The plasma microvesicles, MHV particles and Q-beta bacteriophage particles were then isolated by contacting the sample with a positively charged, spin-filter based capture surface functionalized with quaternary ammonium, as described above.

Nucleic acid was extracted from the microvesicles, MHV particles and Q-beta bacteriophage particles by contacting the capture surface with Qiazol reagent. The eluate was then analyzed using RT-qPCR to determine the CT value for the Q-beta bacteriophage RNA, the MHV RNA, an mRNA that is present in the plasma microvesicles (GAPDH) and a reverse transcription control RNA.

Figure 6:
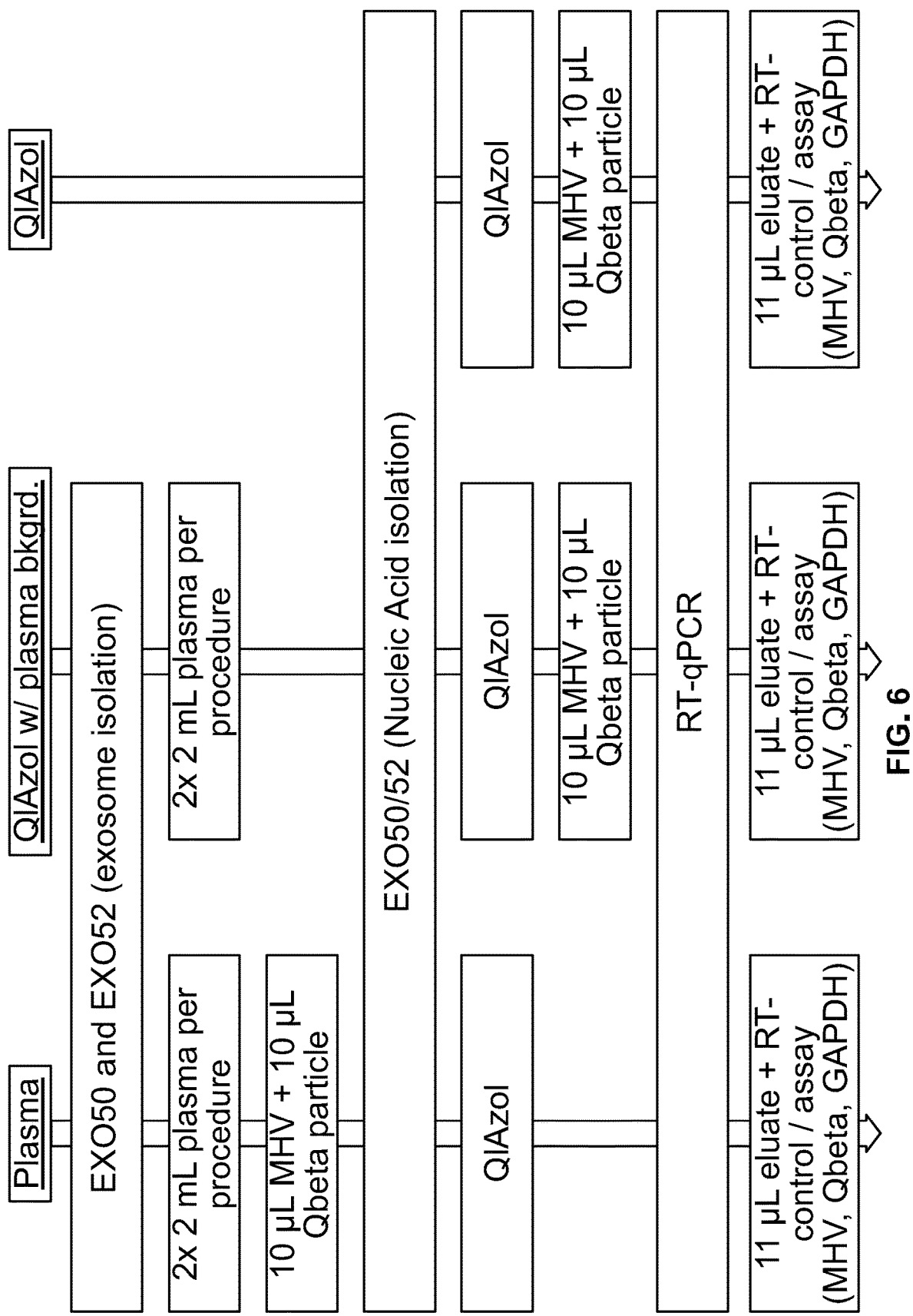
FIG. 6 is a schematic overview of isolation experiments using MHV particles and plasma samples.

In the second experimental condition, referred to as the QIAzol with plasma background (QIAzol w/ palsma bkgrd.) condition in FIG. 6, microvesicles were first isolated from 2 ml plasma samples by contacting the sample with a positively charged, spin-filter based capture surface functionalized with quaternary ammonium, as described above. The isolated microvesicles were then contacted with a mixture 10 µl of a solution comprising MHV particles and 10 µl of a solution comprising Q-beta bacteriophage particles. QIAzol reagent was then added to lyse the isolated microvesicles, MHV particles and Q-beta bacteriophage particles. The eluate was then analyzed using RT-qPCR to determine the CT value for the Q-beta bacteriophage RNA, the MHV RNA, an mRNA that is present in the plasma microvesicles (GAPDH) and a reverse transcription control RNA.

In the third experimental condition, referred to as the QIAzol condition in FIG. 6, a solution comprising 10 µl of a solution comprising MHV particles and 10 µl of a solution comprising Q-beta bacteriophage particles was contacted with QIAzol reagent. The eluate was then analyzed using RT-qPCR to determine the CT value for the Q-beta bacteriophage RNA, the MHV RNA, an mRNA that is present in the plasma microvesicles (GAPDH) and a reverse transcription control RNA.

Figure 7:
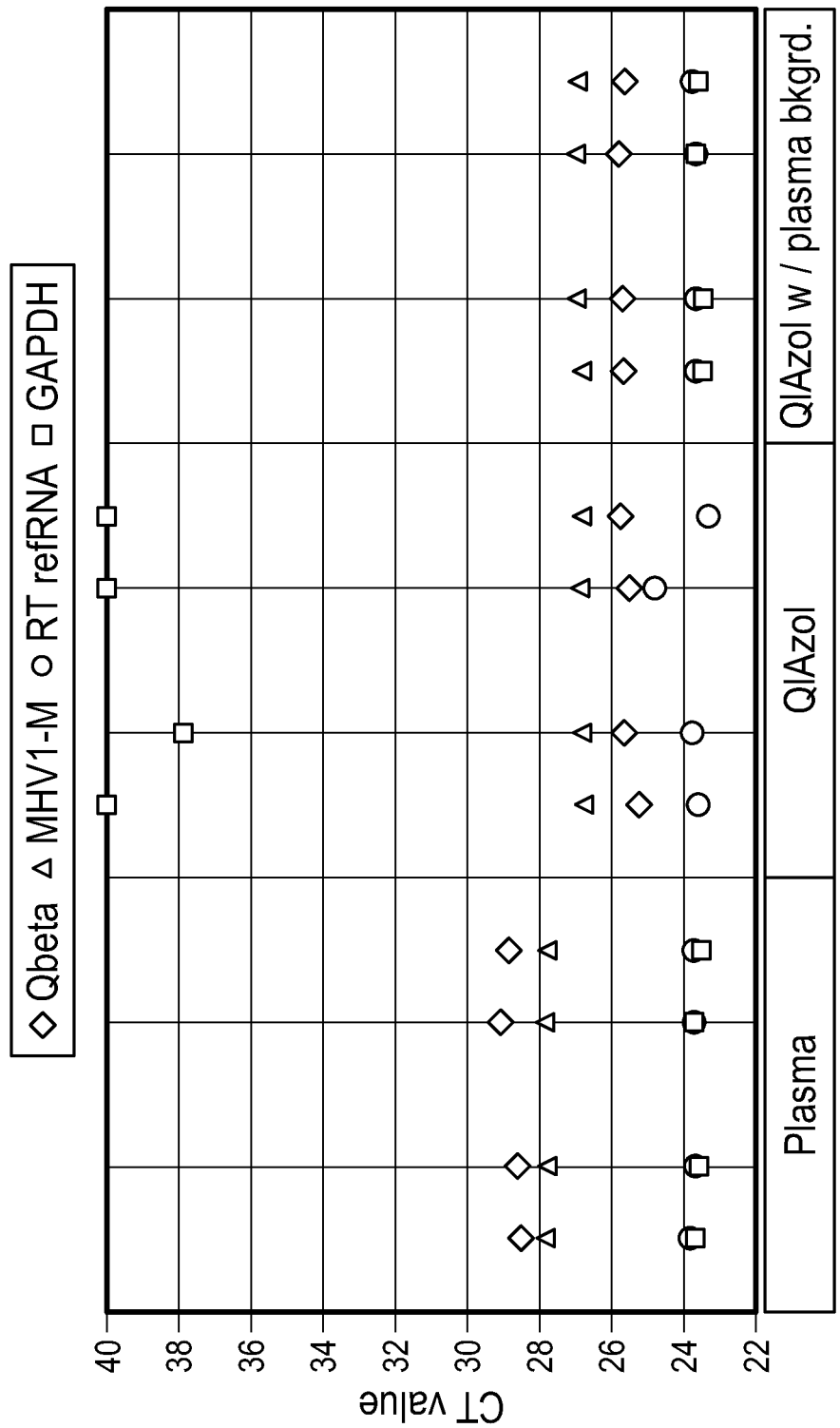
FIG. 7 is a graph showing RT-qPCR results from isolation experiments using MHV particles and plasma samples.

The results of the RT-qPCR analysis in the above experiments are shown in FIG. 7. The results in FIG. 7 show that although both MHV particles and Q-beta bacteriophage particles can be isolated from plasma samples, MHV particles were isolated with a greater efficiency, as evidenced by lower CT values for MHV1 RNA in the Plasma condition. Thus, these results indicate that MHV can be used as a control particle for microvesicle and microvesicular nucleic acid isolation procedures, and that MHV demonstrates superior properties as compared to Q-beta bacteriophage.

Example #4—MHV Isolation Correlates with Microvesicle Isolation Under Conditions with Differing Ionic Strengths The following is an example that demonstrates that the isolation of MHV particles correlates with the isolation of microvesicles under isolation conditions with differing ionic strengths. Importantly, the MHV particle isolation correlated with microvesicle isolation much more strongly than micelle-based alternatives such as RNA extraction Control (REC; Bioline) or protein-based alternatives such as Q-beta bacteriophage particles, indicating that MHV particles exhibit superior properties as an internal control for microvesicle isolation methods.

Figure 8:
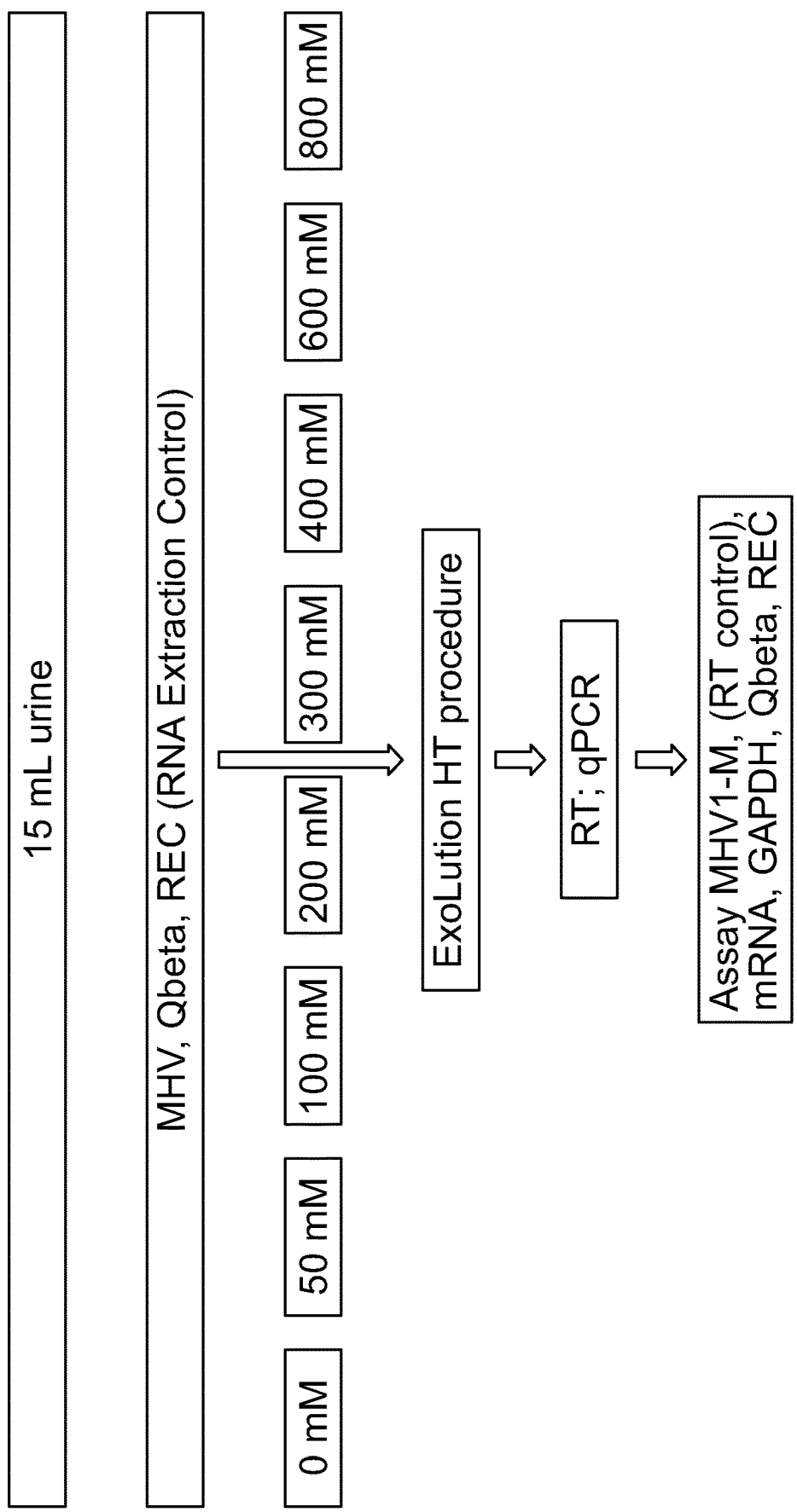
FIG. 8 is a schematic overview of isolation experiments using MHV particles and urine samples at various ionic strengths.

The experimental setup is shown in FIG. 8. Briefly, 15 ml urine samples were mixed with MHV particles, Q-beta bacteriophage particles and REC micelles. The urinary microvesicles, MHV particles, Q-beta bacteriophage particles and REC micelles were then isolated by contacting the sample with a positively charged, bead-based capture surface functionalized with quaternary ammonium, as described above. The isolation was performed at varying ionic strengths, ranging from 0 mM to 800 mM of salt as shown in FIG. 8. Nucleic acids were extracted from the isolated microvesicles, particles and micelles, and the eluate was then analyzed using RT-qPCR to determine the CT value for the Q-beta bacteriophage RNA, the MHV RNA, the REC RNA and an mRNA that is present in the urine microvesicles (GAPDH).

Figure 9:
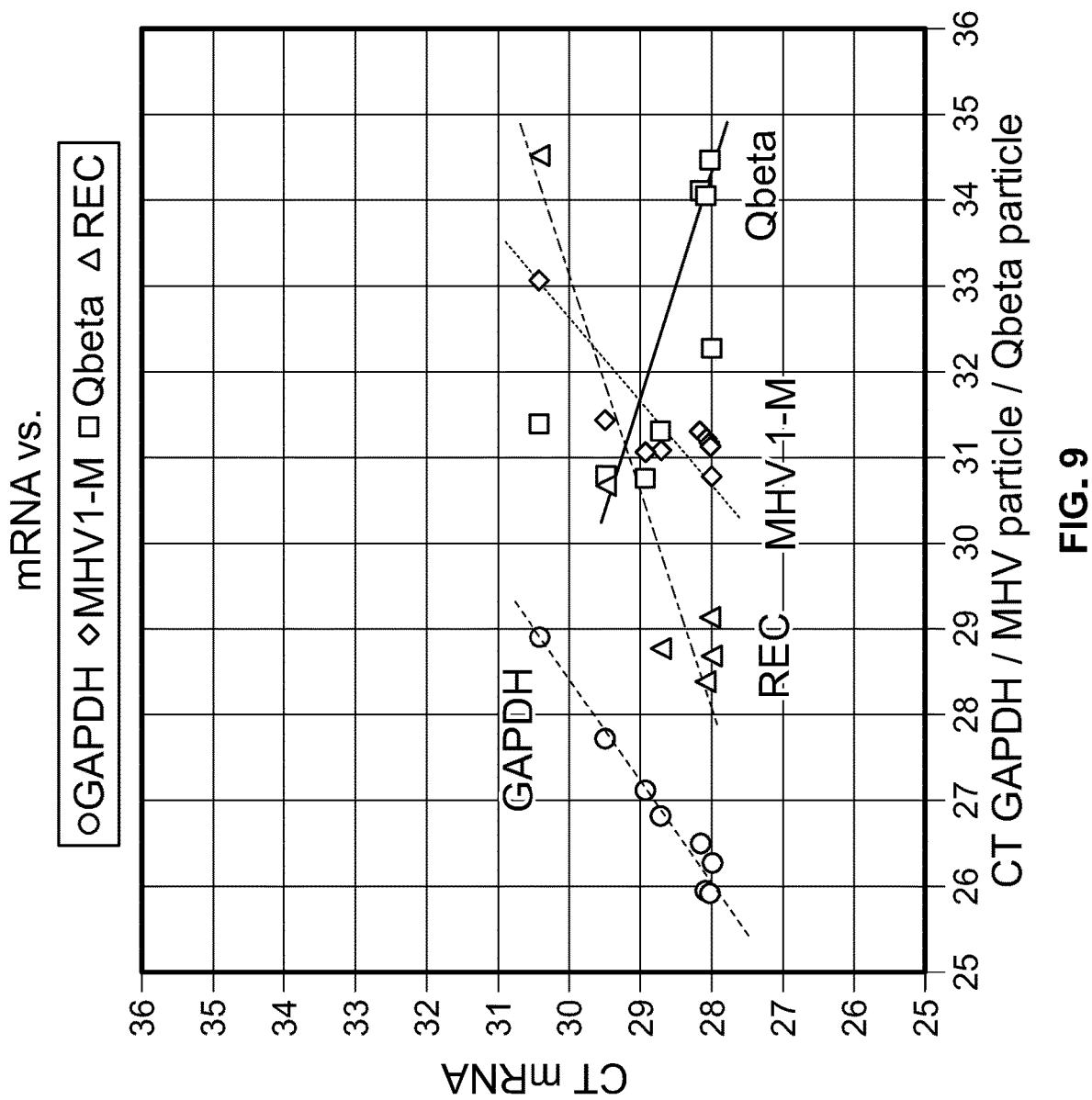
FIG. 9 is a graph showing RT-qPCR results from isolation experiments using MHV particles and urine samples at various ionic strengths.

The results of the RT-qPCR analysis in the above experiments are shown in FIG. 9. The results in FIG. 9 show that the MHV RNA signal correlate well with the exosomal RNA signals as the ionic strength is increased, and that the MHV particle correlation is superior to the correlation shown by REC micelles and Q-beta bacteriophage particles.

Example #5—MHV Contains RNA that is Protected from RNAses by a Lipid Membrane

The following is an example that demonstrates that MHV particles are similar to exosomes in that MHV particles contain RNA that is protected from RNAses by a lipid membrane.

Figure 10:
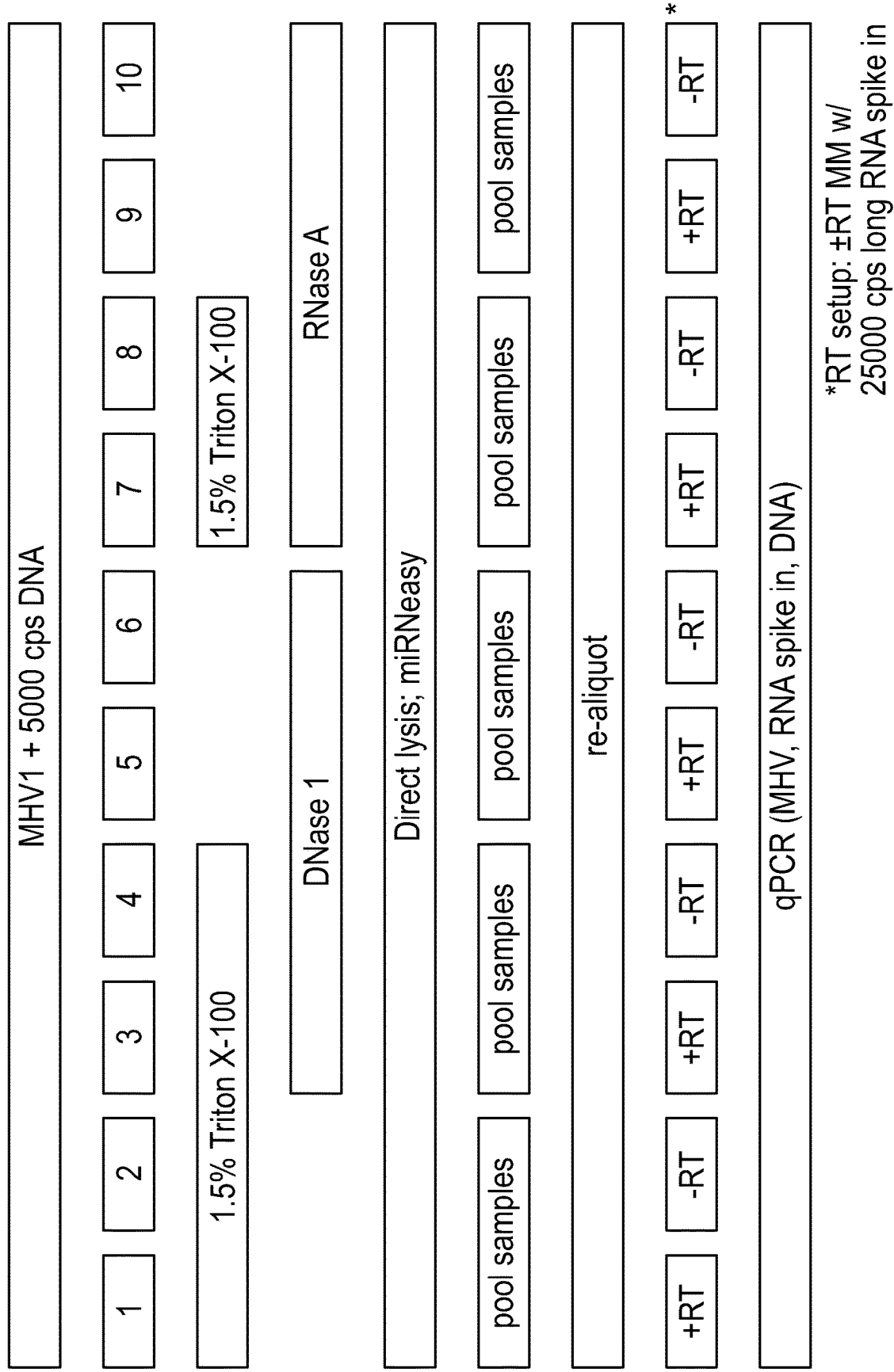
FIG. 10 is a schematic overview of DNase and RNase protection assays using MHV particles.

The experimental setup is shown in FIG. 10. Briefly, a starting mixture of MHV1 particles and 5000 copies of a first control DNA molecule were treated with various combinations of 1.5% Triton X-100, DNase 1 and RNase A. Each condition was tested in duplicate. The treated samples were then lysed, the RNA purified, and finally analyzed using RT-qPCR. An additional 25000 copies of a long RNA control was added during the reverse transcription reaction.

Figure 11:
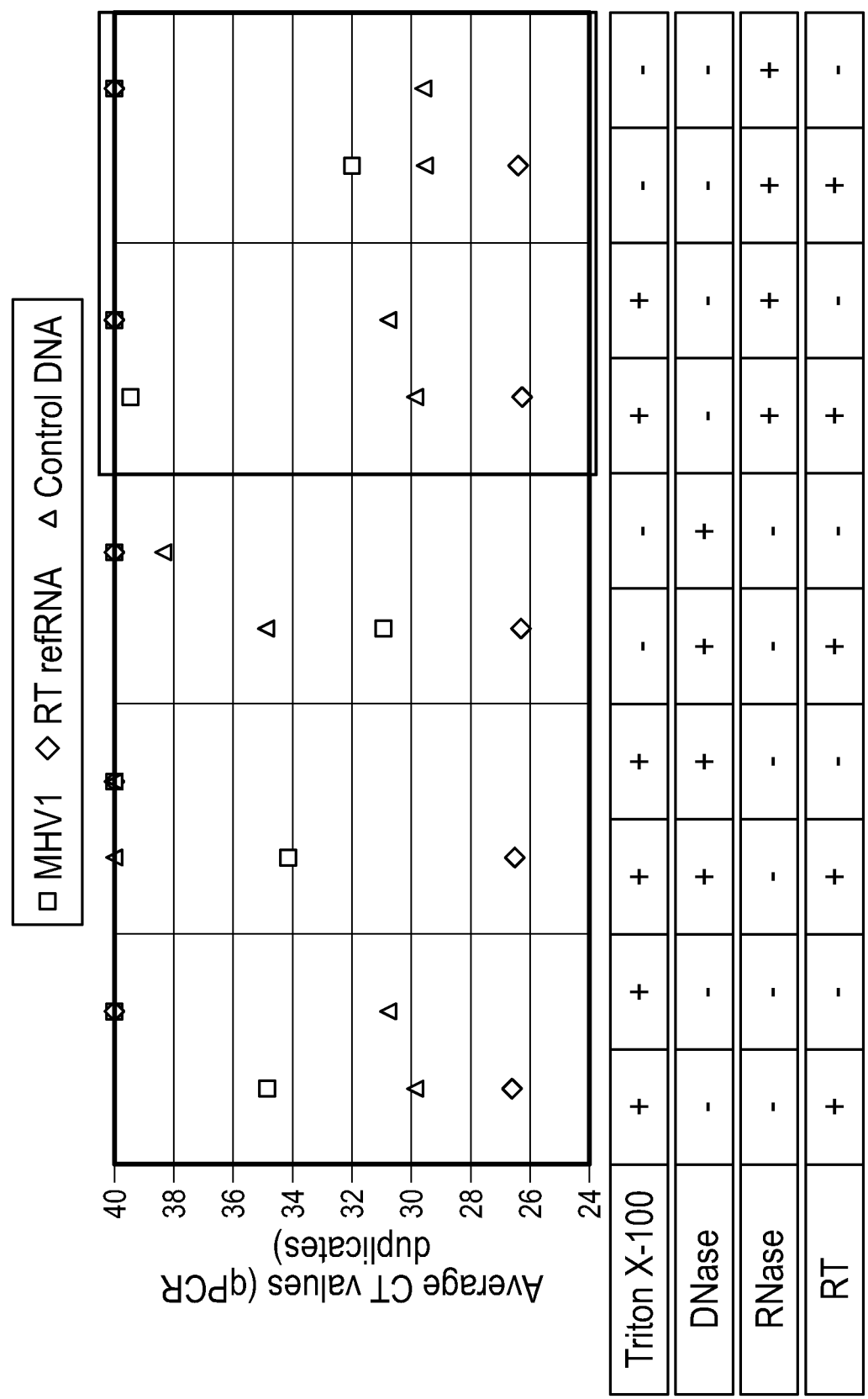
FIG. 11 is a graph showing RT-qPCR results from DNase and RNase protection assays using MHV particles.

The results of this experiment are shown in FIG. 11. The results in FIG. 11 demonstrate that MHV particles contain lipid enveloped RNA cargo, as MHV signals cannot be detected without reverse transcription, and RNAse treatment only shows an impact when combined with a detergent treatment. Furthermore, MHV particles are not impaired by DNase treatment.

Figure 12:
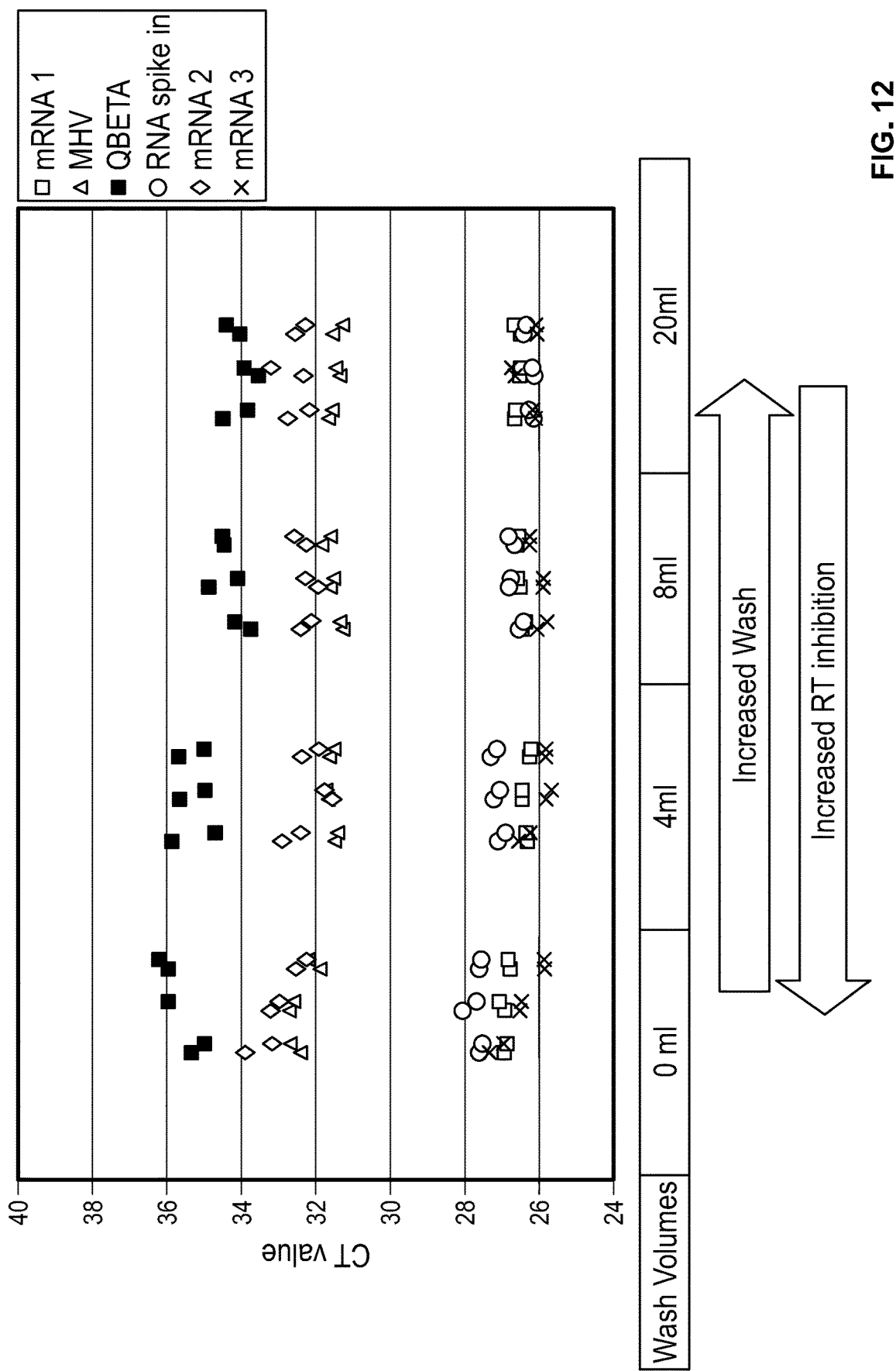
FIG. 12 is a graph showing RT-qPCR results from isolation experiments using MHV particles and various wash buffer volumes.

Example #6—Isolation of MHV Particles Reflects the Amount of Reverse Transcription Inhibitors that are Co-Purified During Isolation Decreased washing during microvesicle isolation is known to increase reverse transcriptase inhibition in downstream analysis, as the isolation results in increased co-purification of reverse transcriptase inhibitors. In this example, biological samples were first mixed with MHV particles and Q-beta particles. The microvesicles from the biological sample, along with the MHV particles and the Q-beta particles were then isolated using various amounts of washing during isolation, ranging from 0 ml of wash buffer (no washing) to 20 ml of wash buffer. Nucleic acids were then extracted from the microvesicles, MHV particles and Q-beta particles, and the extracted nucleic acids were analyzed using RT-qPCR. The results of the RT-qPCR analysis is shown in FIG. 12. The results shown in FIG. 12 show that with less washing, the CT values for the microvesicular mRNAs (mRNA 1, mRNA 2 and mRNA 3) were increased, which is indicative of reverse transcription inhibition. MHV RNA showed a similar increase in measured CT value. These results indicate that the co-isolation of MHV particles can detect the purification of reverse transcriptase inhibitors, making MHV particles a powerful internal control for isolation procedures.

Example #7—MHV can be Isolated Quantitatively and in a Scalable Fashion Using a Filtration-Based Isolation Method The following is an example that demonstrates that MHV particles can be co-isolated with microvesicles from biological samples using filtration-base isolation methods.

Figure 13:
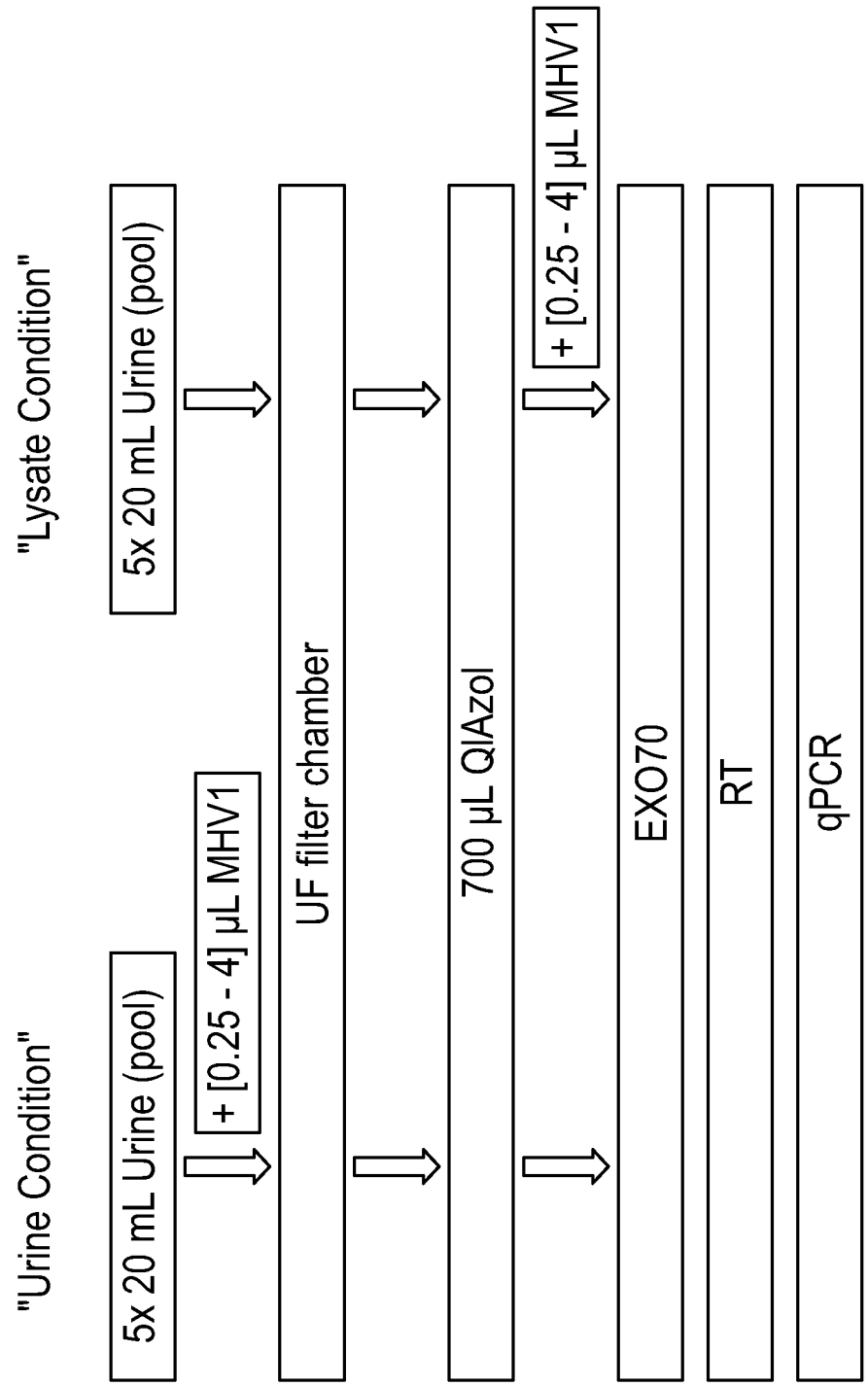
FIG. 13 is a schematic overview of isolation experiments using MHV particles and urine samples.

The experimental set up is shown in FIG. 13. Briefly, two different experimental conditions were tested. In the first experimental condition, referred to as the Urine condition in FIG. 13, five, 20 mL Urine samples were mixed with various amounts of a solution comprising MHV particles ranging from 0.25 µl to 4 µl. The urinary microvesicles and the MHV particles were then isolated using an ultrafiltration (UF) filter chamber. The isolated microvesicles and MHV particles were then lysed using 700 µl of QIAzol reagent and the microvesicular and MHV nucleic acids were purified and analyzed using RT-qPCR.

In the second experimental condition, referred to as the Lysate condition in FIG. 13, microvesicles from 5, 20 mL urine samples were first isolated using an ultrafiltration (UF) filter chamber. The isolated microvesicles were then lysed by contacting them with QIAzol reagent. Various amounts of a solution comprising MHV particles (ranging from 0.25 µl to 4 µl) were then added to the lysis reaction. Any released nucleic acid was then purified analyzed using RT-qPCR.

Figure 14:
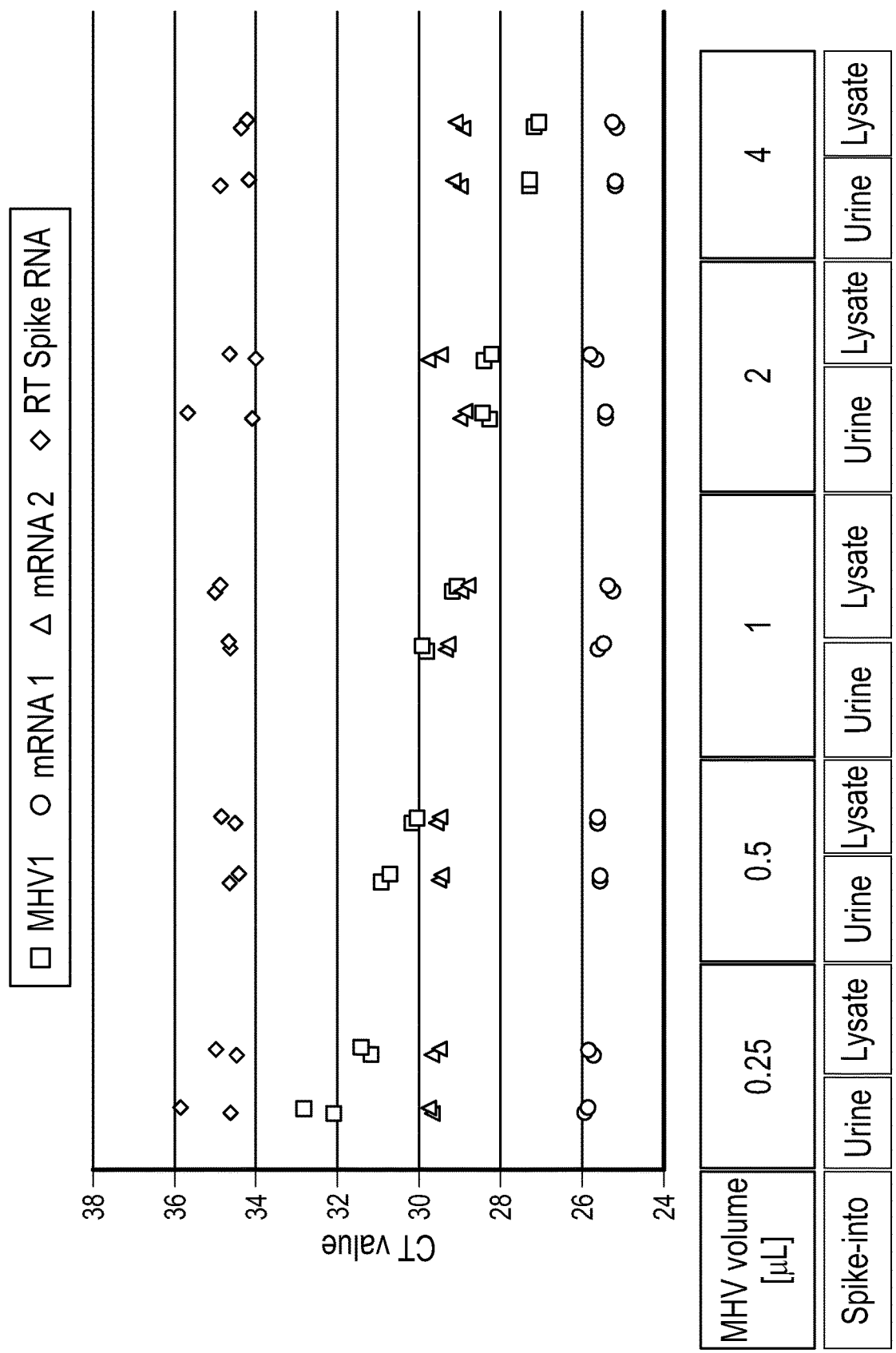
FIG. 14 is a graph showing RT-qPCR results from isolation experiments using MHV particles and urine samples.

The results of the RT-qPCR analysis in the above experiments are shown in FIG. 14. The results in FIG. 14 demonstrate that the MHV particles can be co-isolated with microvesicles using a filtration-based isolation method and that all tested amounts of MHV particles could be detected.

Figure 15:
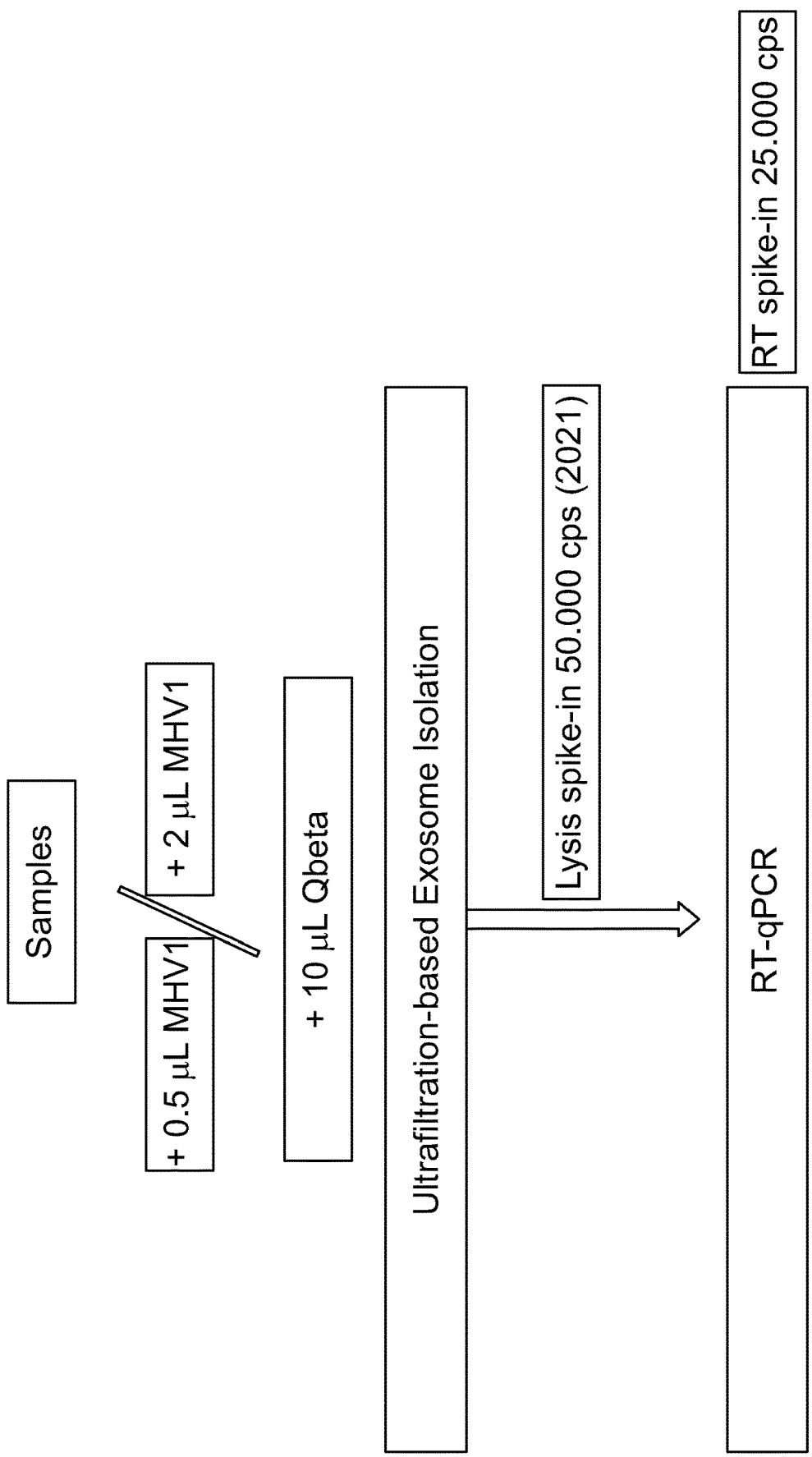
FIG. 15 is a schematic overview of isolation experiments using MHV particles.
Figure 16:
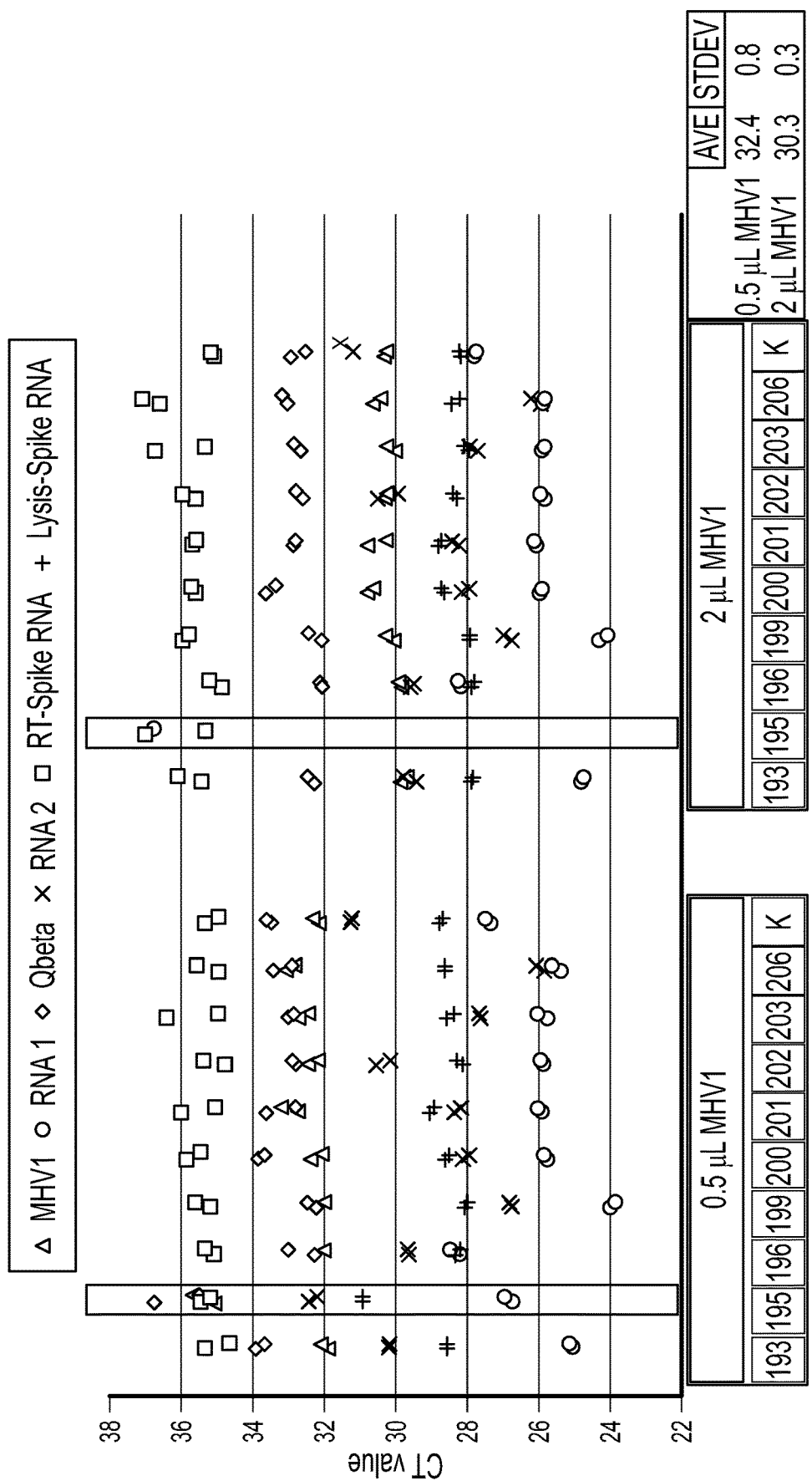
FIG. 16 is a graph showing RT-qPCR results from isolation experiments using MHV particles.

Example #8—MHV Particles can be Used to Interrogate Nucleic Acid Isolation Failures in Microvesicle Isolation Protocols The following is an example that demonstrates that MHV particles can be used as part of a microvesicle isolation process to inform the user to a nucleic acid isolation failure. The experimental setup is shown in FIG. 15. Briefly, urine samples were mixed with either 0.5 µl of a solution comprising MHV particles or 2 µl of a solution comprising MHV particles. 10 µl of a solution comprising Q-beta bacteriophage particles was also added to the urine samples. The urinary microvesicles, MHV particles and Q-beta bacteriophage particles were then isolated using an ultrafiltration-based isolation protocol. Lysis reagent to extract the nucleic acids from the isolated urinary microvesicles, MHV particles and Q-beta bacteriophage particles. During lysis, 50,000 copies of a control RNA (Lysis-spike RNA) were also added to each sample. The extracted nucleic acids were then isolated and analyzed using RT-qPCR. The RT-qPCR analysis included the spike-in of 25,000 copies of a reverse transcription control RNA (RT-spike RNA). The results of the experiment are shown in FIG. 16. The results from two of the samples are boxed in FIG. 16. In these boxed samples, there was a failure in the nucleic acid isolation step, as there was no inhibition of the reverse transcription reaction (RT-spike RNA was detected normally) but the Lysis-Spike RNA shows impairment. The MHV RNA signal shows the same impairment as the Lysis-Spike RNA, indicating that the MHV control particle can inform a user as to a failure in nucleic acid isolation as part of a larger microvesicular nucleic acid isolation protocol.

Example #9—MHV Particles are Stable in Biological Samples

Figure 17:
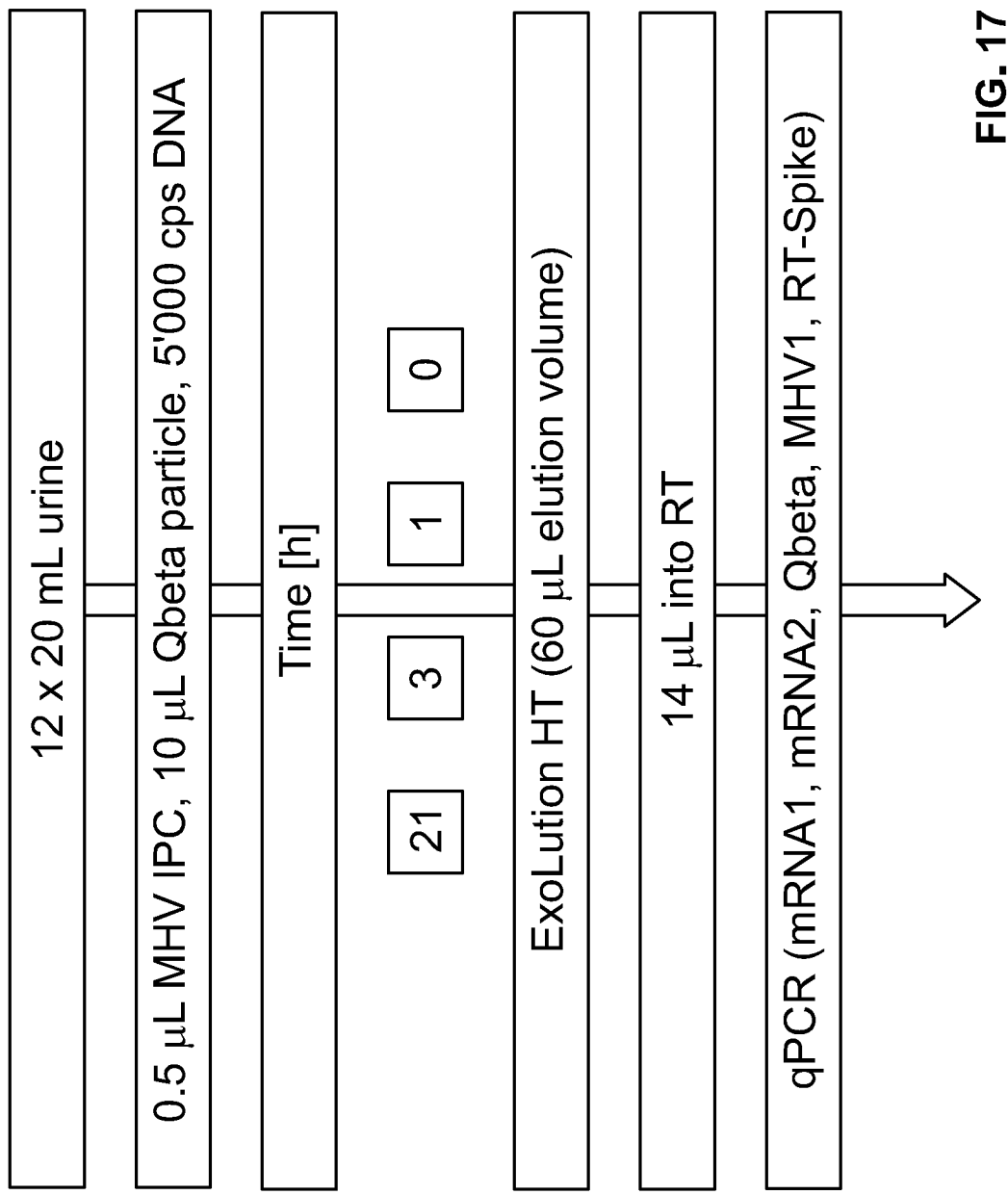
FIG. 17 is a schematic overview of isolation experiments using MHV particles incubated in urine samples for various lengths of time.
Figure 18:
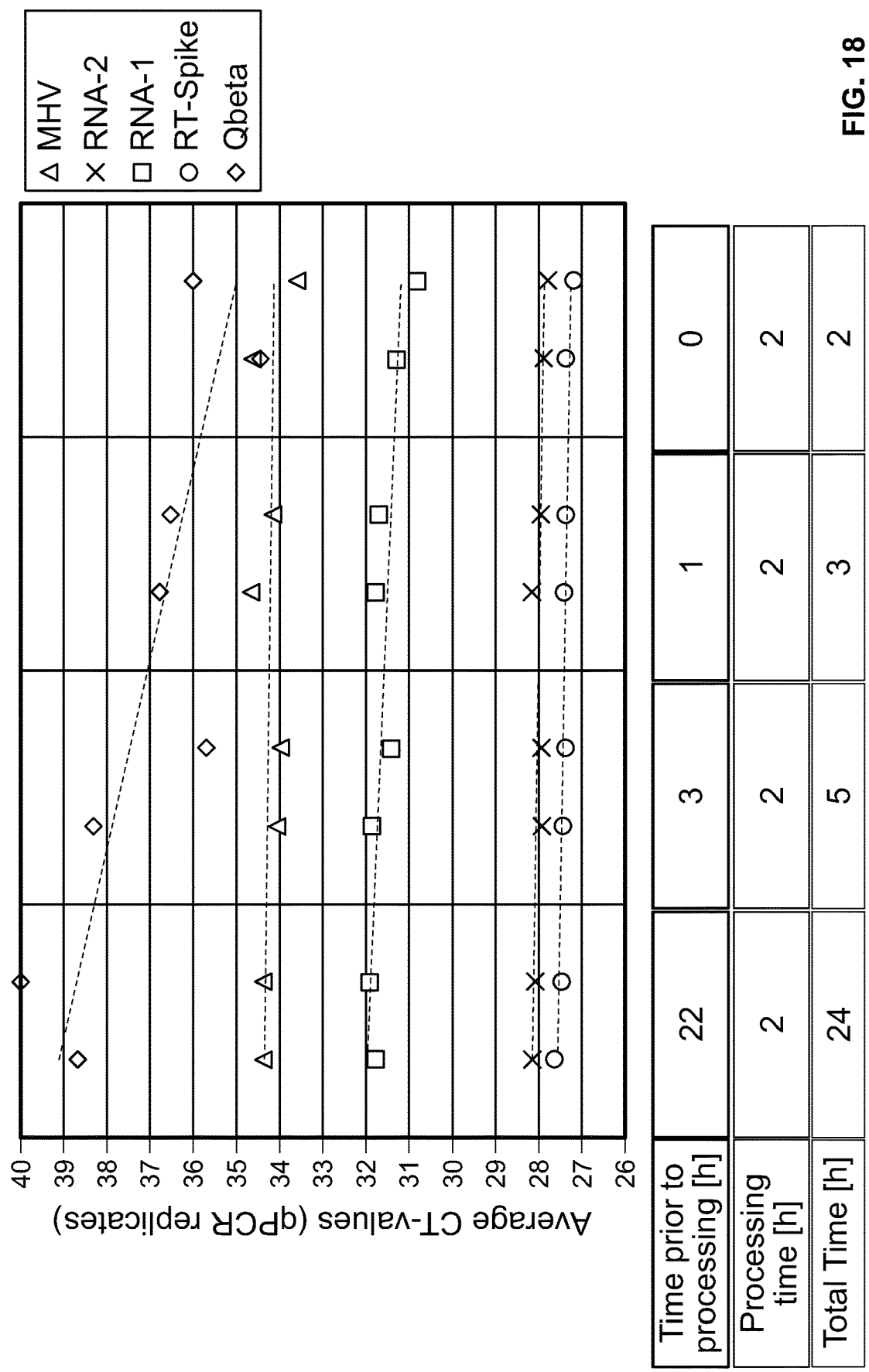
FIG. 18 is a graph showing RT-qPCR results of isolation experiments using MHV particles incubated in urine samples for various lengths of time.

Turnaround times of various biological assays can vary. For example, the processing and analysis of microvesicles from a 96-well plate containing urine samples could take up to 13 hours. This means that some of the samples have to wait up to 10.5 hours prior to the start of processing. Thus, any control particle that is added to the samples must be stable for extended periods of time, upwards of more than 12 hours. The following example demonstrates that MHV particles are stable in biological samples, including urine samples. The experimental setup is shown in FIG. 17. Briefly, 20 ml urine samples were mixed with 0.5 µl of a solution comprising MHV particles, 10 µl of a solution comprising Q-beta bacteriophage particles and/or 5,000 copies of a control nucleic acid. These samples were then incubated for various times ranging from 21 hours to 0 hours (processing began after mixing of control particles and urine sample). The control particles (MHV particles, Q-beta bacteriophage partcles), the urinary microvesicles and the control nucleic acid were then isolated by contacting the samples with a positively charged, bead-based capture surface functionalized with quaternary ammonium, as described above. The nucleic acid was then extracted and analyzed using RT-qPCR. A control RNA was added to the reverse transcription reaction (RT-spike). The results of the RT-qPCR are shown in FIG. 18. The results in FIG. 18 show that there was no deterioration in signal for the MHV RNA, indicating that the MHV particles were stable over all incubation times. In contrast, there was significant loss of signal for the Q-beta bacteriophage RNA, indicating that Q-beta bacteriophage is significantly less stable in biological samples than the MHV particles.

Example #10—MHV can be Isolated from Reproducibly Isolated from Biological Samples Using a Variety of Methods The following is an example that demonstrates that MHV particles can be reproducibly isolated from biological samples using a variety of different methods, and that the isolation of MHV particles exhibits less variation than a protein-based alternative such as Q-beta bacteriophage particles.

Figure 19:
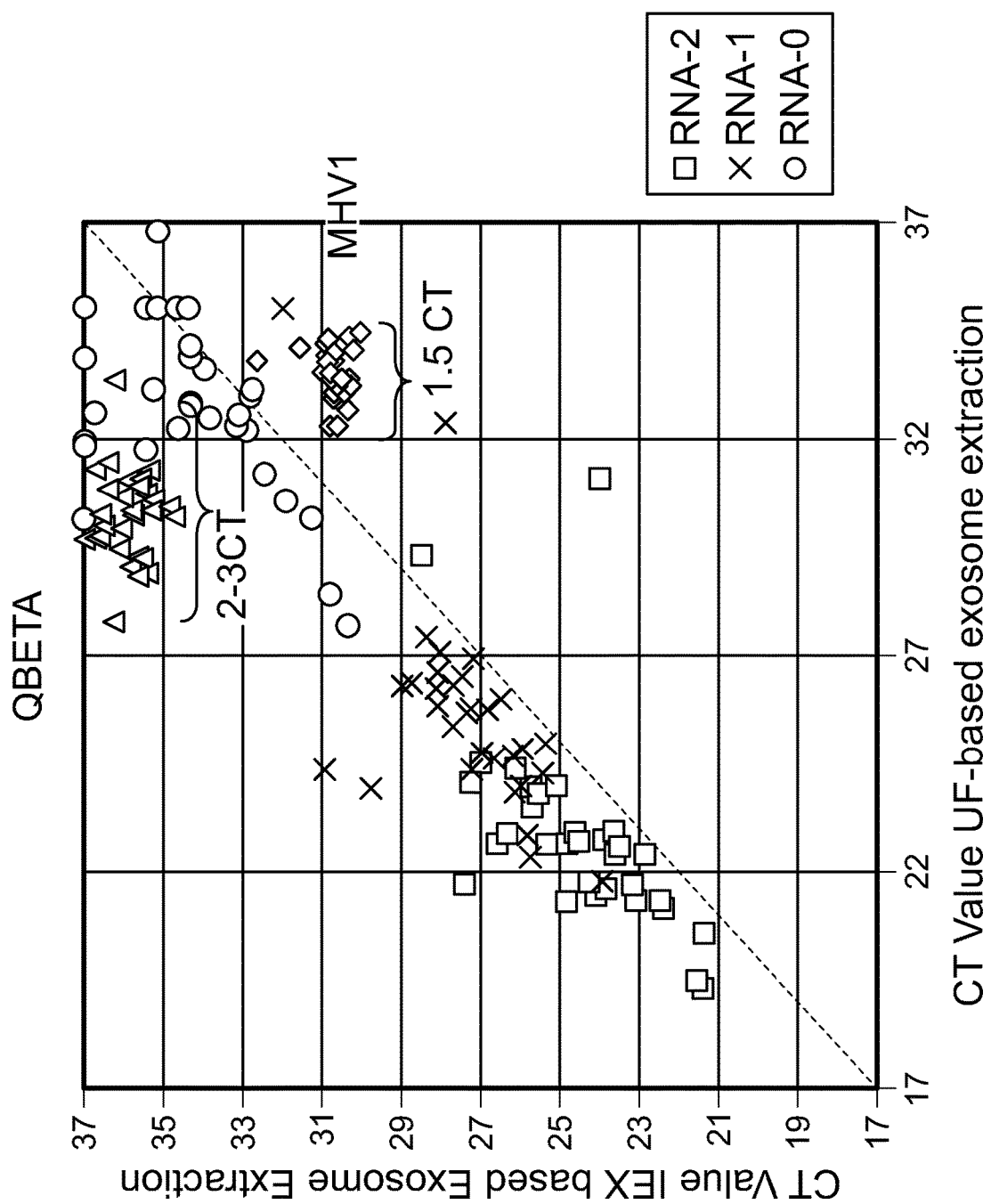
FIG. 19 is a graph showing RT-qPCR results of isolation experiments using MHV particles.

In this example, 32 different 15 ml urine samples were spiked with MHV particles and Q-beta bacteriophage particles. The MHV particles and the Q-beta bacteriophage particles were then isolated from the urine samples using either ultrafiltration (UF) methods or bead-based ion-exchange (IEX) methods. Nucleic acid was then extracted from the isolated particles and analyzed using RT-qPCR. As shown in FIG. 19, MHV particles exhibited significantly less variation in measured CT values, demonstrating that it exhibits superior properties as a control particle as compared to Q-beta bacteriophage.

Example #11—Enveloped Virus Particles can be Co-Isolated with Microvesicles from Biological Samples The following is an example demonstrating that other enveloped viruses such as bovine viral diarrhea virus (BVDV) can be co-isolated with microvesicles from a biological sample and thus can be used as an internal control. In the following experiments, in addition to their native genome, the BVDV particles also comprised a portion of a human virus (HCV).

Three experimental conditions were tested. In the first experimental condition, 25 µl of a solution comprising the BVDV particles was added to 10 ml of PBS. The BVDV particles were then isolated using microvesicle isolation methods described herein. This condition is referred to as the "HCV/BVDV in PBS then exosome extraction" condition. The isolated BVDV particles were then contacted with QIAzol reagent to extract the nucleic acids. The extracted nucleic acids were then analyzed using RT-qPCR to determine a CT value for an mRNA preset in urinary microvesicles (GAPDH), various BVDV RNAs (BVDV-Z, BVDV-H and BVDV-NS3) and the HCV RNA. A control RNA was also added to the reverse transcription reaction (RNA spike-in) and analyzed.

In the second experimental condition, 25 μl of a solution comprising the BVDV particles was added to 10 ml of a urine sample. The urinary microvesicles and BVDV particles were then isolated using microvesicle isolation methods described herein. This condition is referred to as the "HCV/BVDV in urine then exosome extraction" condition. The isolated urinary microvesicles and BVDV particles were then contacted with QIAzol reagent to extract the nucleic acids. The extracted nucleic acids were then analyzed using RT-qPCR to determine a CT value for an mRNA preset in urinary microvesicles (GAPDH), various BVDV RNAs (BVDV-Z, BVDV-H and BVDV-NS3) and the HCV RNA. A control RNA was also added to the reverse transcription reaction (RNA spike-in) and analyzed.

In the third experimental condition, varying amounts (3.1 μl to 100 μl) of a solution comprising the BVDV particles were added directly to QIAzol reagent. To extract the nucleic acids from the BVDV particles. This condition is referred to as the "HCV/BVDV direct lysis in QIAzol" condition. The extracted nucleic acids were then analyzed using RT-qPCR to determine a CT value for an mRNA preset in urinary microvesicles (GAPDH), various BVDV RNAs (BVDV-Z, BVDV-H and BVDV-NS3) and the HCV RNA. A control RNA was also added to the reverse transcription reaction (RNA spike-in) and analyzed.

Figure 20:
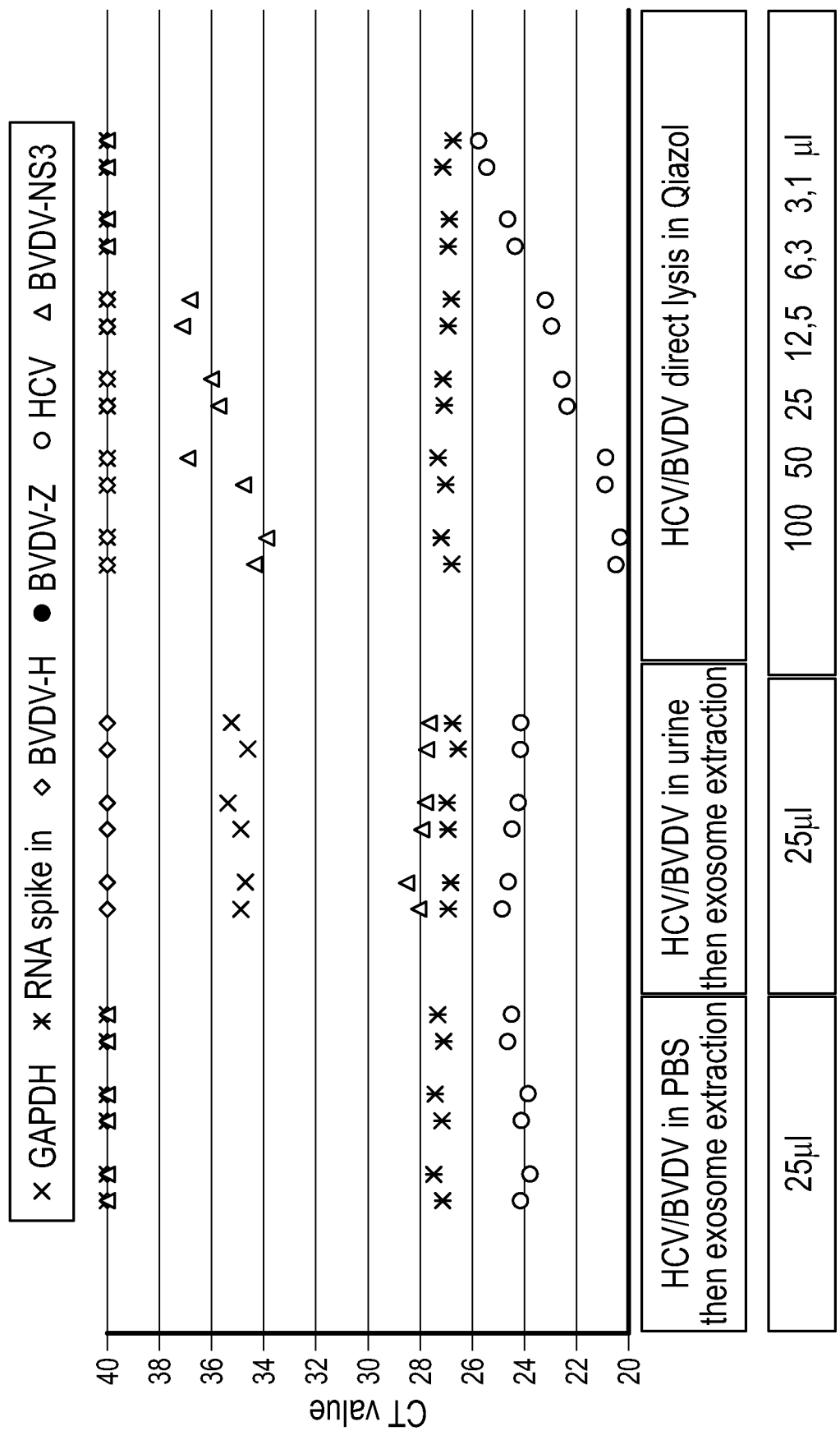
FIG. 20 is a graph showing RT-qPCR results of isolation experiments using BVDV particles.

The results of the RT-qPCR analysis in the above experiments are shown in FIG. 20. The results in FIG. 20 show that the BVDV particles can be co-isolated with microvesicles in a biological sample, and the nucleic acid cargo of the BVDV particles can be detected. Thus, enveloped virus particles such as BVDV and MHV can be used as internal controls for microvesicle isolation methods.

What is claimed is:

1. A method comprising:
   (a) adding a known quantity of control particles comprising at least one control nucleic acid and/or at least one control protein to a biological sample, wherein the control particles comprise a non-human animal enveloped virus, wherein the non-human animal enveloped virus is selected from mouse hepatitis virus (MHV), bovine diarrhea virus (BVDV) and transmissible gastroenteritis coronavirus (TGEV);
   (b) isolating microvesicles and the control particles from the biological sample;
   (c) extracting nucleic acids and/or protein from the microvesicles and the control particles;
   (d) assaying the amount of the at least one control nucleic acid and/or the at least one control protein recovered, thereby determining the amount of control particles recovered;
   (e) determining that the amount of control particles calculated in step (d) is within a predetermined range of values; and
   (f) subjecting the nucleic acids and/or protein from step (c) to further analysis if the amount of control particle calculated in step (d) is within the predetermine range of values;
   wherein the isolating of the microvesicles and control particles from the biological sample comprises contacting the biological sample with a capture surface under conditions sufficient to retain cell-free DNA, microvesicles, and control particles on the capture surface, and wherein the capture surface comprises one or more beads that are positively charged, one or more beads that are an anion exchanger functionalized with quaternary ammonium (R—CH$_2$—N$^+$(CH$_3$)$_3$), or one or more beads that are positively charged and functionalized with quaternary ammonium.

2. The method of claim 1, wherein the non-human animal enveloped virus is an inactivated non-human animal enveloped virus.

3. The method of claim 1, wherein the biological sample is a bodily fluid sample, wherein the bodily fluid sample comprises urine, blood, cerebrospinal fluid, serum or any combination thereof.

4. The method of claim 1, wherein the at least one control nucleic acid comprises RNA.

5. The method of claim 1, wherein the nucleic acids from step (c) comprises RNA, DNA, or RNA and DNA.

6. The method of claim 1, wherein assaying the amount of the at least one control nucleic acid recovered comprises determining the expression level or copy number of the control nucleic acid.

7. The method of claim 6, wherein assaying the expression level or copy number of the control nucleic acid comprises reverse transcribing the control nucleic acid, quantitative PCR (qPCR), or any combination thereof.

8. The method of claim 1, wherein step (f) further comprises determining the presence, absence or level of at least one biomarker associated with a disease or medical condition for diagnosing, prognosing, or monitoring the disease or medical condition.

9. The method of claim 8, wherein determining the presence, absence or level of at least one biomarker associated with a disease or medical condition for diagnosing, prognosing, or monitoring the disease or medical condition comprises reverse transcription, quantitative PCR, or any combination thereof.

10. A method comprising:
    (a) isolating microvesicles from a biological sample;
    (b) adding a known quantity of control particles comprising at least one control nucleic acid and/or at least one control protein to the isolated microvesicles, wherein the control particles comprise a non-human animal enveloped virus, wherein the non-human animal enveloped virus is selected from mouse hepatitis virus (MHV), bovine diarrhea virus (BVDV) and transmissible gastroenteritis coronavirus (TGEV);
    (c) extracting nucleic acids and/or protein from the isolated microvesicles and the control particles;
    (d) assaying the amount of the at least one control nucleic acid and/or the at least one control protein recovered, thereby determining the amount of control particles recovered;
    (e) determining that the amount of control particles calculated in step (d) is within a predetermined range of values; and
    (f) subjecting the nucleic acids and/or protein from step (c) to further analysis if the amount of control particle calculated in step (d) is within the predetermine range of values;
    wherein the isolating of the microvesicles and control particles from the biological sample comprises contacting the biological sample with a capture surface under conditions sufficient to retain cell-free DNA, microvesicles, and control particles on the capture surface, and wherein the capture surface comprises one or more beads that are positively charged, one or more beads that are an anion exchanger functionalized with quaternary ammonium ($R-CH_2-N^+(CH_3)_3$), or one or more beads that are positively charged and functionalized with quaternary ammonium.

11. The method of claim 10, wherein the non-human animal enveloped virus is an inactivated non-human animal enveloped virus.

12. The method of claim 10, wherein the biological sample is a bodily fluid sample, wherein the bodily fluid sample comprises urine, blood, cerebrospinal fluid, serum or any combination thereof.

13. The method of claim 10, wherein the at least one control nucleic acid comprises RNA.

14. The method of claim 10, wherein the nucleic acids from step (c) comprises RNA, DNA, or RNA and DNA.

15. The method of claim 10, wherein assaying the amount of the at least one control nucleic acid recovered comprises assaying the expression level or copy number of the control nucleic acid.

16. The method of claim 15, wherein assaying the expression level or copy number of the control nucleic acid comprises reverse transcribing the control nucleic acid, quantitative PCR (qPCR), or any combination thereof.

17. The method of claim 10, wherein step (f) further comprises determining the presence, absence or level of at least one biomarker associated with a disease or medical condition for diagnosing, prognosing, or monitoring the disease or medical condition.

18. The method of claim 7, wherein the quantitative PCR is reverse transcription quantitative PCR (RT-qPCR).

19. The method of claim 16, wherein the quantitative PCR is reverse transcription quantitative PCR (RT-qPCR).

* * * * *